(12) United States Patent
Lin

(10) Patent No.: US 6,677,350 B1
(45) Date of Patent: Jan. 13, 2004

(54) BETA-FLUOROETHYL THIOUREA COMPOUNDS AND USE

(75) Inventor: Yuh-Meei Lin, Naperville, IL (US)

(73) Assignee: Advanced Life Sciences, Inc., Woodridge, IL (US)

( * ) Notice: Subject to any disclaimer, the term of this patent is extended or adjusted under 35 U.S.C. 154(b) by 0 days.

(21) Appl. No.: 09/667,131

(22) Filed: Sep. 21, 2000

Related U.S. Application Data

(60) Provisional application No. 60/155,519, filed on Sep. 22, 1999.

(51) Int. Cl.$^7$ ............................................. A61K 31/44
(52) U.S. Cl. .................................................... 514/298
(58) Field of Search ........................................ 514/298

(56) References Cited

U.S. PATENT DOCUMENTS

| | | | | |
|---|---|---|---|---|
| 4,273,776 A | * | 6/1981 | Hoehm ........................ | 424/263 |
| 5,354,866 A | | 10/1994 | Kempf et al. ................. | 546/265 |
| 5,650,433 A | | 7/1997 | Watanabe et al. ............. | 514/456 |

FOREIGN PATENT DOCUMENTS

| | | |
|---|---|---|
| DE | 3544457 A1 | 12/1985 |
| EP | 0 004 579 A1 | 10/1979 |
| EP | 0 427 026 B1 | 5/1991 |
| JP | 87200570 | 8/1987 |
| JP | 89207203 | 8/1989 |
| JP | 1221314 | 9/1989 |
| WO | WO 93/17671 | 9/1993 |
| WO | WO 95/06628 | 3/1995 |
| WO | WO 97/00679 | 1/1997 |
| WO | WO 98/36750 | 8/1998 |
| WO | WO 98/44920 | 10/1998 |
| WO | WO 98/46238 | 10/1998 |
| WO | WO 99/00114 | 1/1999 |

OTHER PUBLICATIONS

Aach, R. D. The treatment of chronic type B viral hepatitis. *Ann. Intern. Med.* 1988, 109, 89–91.

Alexander, G. J.; Brahm, J.; Fagan, E. A.; Smith, H. M.; Daniels. H. M.; Eddleston, A. L.; Williams, R., Loss of HBSAg with interferon therapy in chronic hepatitis B virus infection. *Lancet* 1987, ii, 66–69.

Arya, Ranjiana; Babu, Vikas: Ilyas, M.; Nasim, K.T. Phytochemical examination of the leaves of *Anaeardium occidentale*. *J. Indian Chem. Soc.*, 1989, 66, 67–68.

Anand, K.K.; Gupta, V.N.; Rangari, V.; Singh, B.; Chandan, B.K. Structure and hepatoprotective activity of a biflavonoid from *Ganarium manii*. *Planta Medica*, 1992, 58, 493–495.

Bardos, T.J.; Schinazi, R.F. Ling, K.–H.; Heider, A.R. Structure–activity relationships and mode of action of 5–mercapto–substituted oligo– and polynucleotides as antitemplates inhibiting replication of human immunodeficiency virus type 1. *Antimicrob. Agents Chemother.*, 1992, 36, 108–114.

Barre, Sinoussi, F.; Chermann, J.C.; Rey, R.; Nugeyre, L.M.T.; Chamaret, S.; Gruest, J.; Dauguet, C.; Axler–Blin, C.; Vezinet–Brun, F.; Rouzioux, C.; Rozenbaum, W., and Montagnier, L. Isolation of a T–lymphotopic retrovirus from a patient at risk for acquired immune deficiency syndrome (AIDS). *Science,* 1983, 220, 868–871.

(List continued on next page.)

*Primary Examiner*—Kevin E. Weddington
(74) *Attorney, Agent, or Firm*—McDonnell Boehnen Hulbert & Berghoff

(57) ABSTRACT

The present invention relates to compounds, compositions and methods for the prevention or treatment of mycobacterium infections. The compounds are naturally occurring and synthetic biflavonoids, flavonoids, chalcones and chalcone like compounds. The compounds were screened for antimycobacterium activity. Of the compounds showing antimycobacterium activity, eight were identified as particularly potent, exhibiting greater than 90% inhibition of the growth of Mtb at a concentration of 12.5 μg/mL. The actual minimum inhibitory concentrations (MIC), defined as the lowest concentration inhibiting 99% of the inoculum, for the preferred compounds ranged from 6.8 to 48.3 μM.

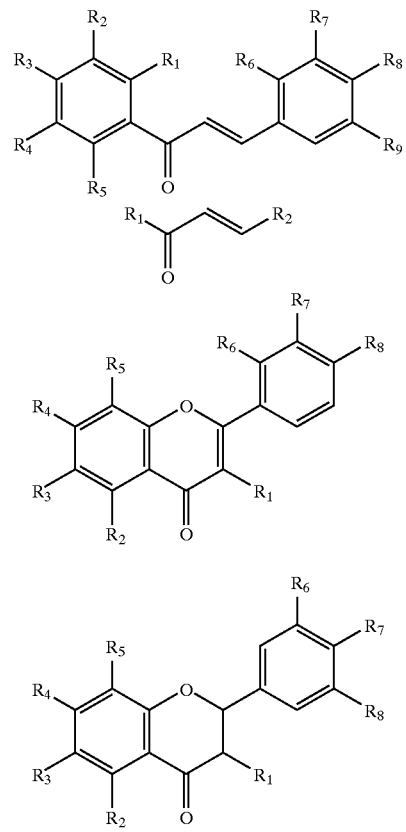

15 Claims, No Drawings

OTHER PUBLICATIONS

Barron, D.; Ibrahim, R.K. Synthesis of flavanoid sulfates: 1. stepwise sulfaction of position, 3,7, and 4' using N,N'–dicyclohexycarbodiimide and tetrabutylamminium hydrogen sulfate. *Tetrahedron,* 1987, 43, 5197–5202.

Bryson, Y. J.; Monahan, C.; Pollack, M.; Shields, W. D. A prospective double–blind study of side effects associated with the administration of amantadine for influenza A virus prophylaxis. *J. Infect. Dis.* 1980, 141, 543–547.

Chen, F.C.; Lin, Y.M.; Hung, J.C. A new biflavanone glucoside from *Garcinia multiflora. Phytochemistry,* 1975C, 14, 818–820.

Chen, F.C.; Lin, Y.M.; Liang, C.M. Biflavonyls from drupes of *Rhus succedanea. Phytochemistry,* 1974A, 12, 276–277.

Chen, F.C.; Lin, Y.M. Rhusflavanone, a new biflavanone from the seeds of wax tree. *J. Chem. Soc., Perkin Trans.,* 1976, I, 98–101.

Chen, F.C.; Lin, Y.M. Succedaneaflavanone—A new 6,6"–biflavanone from Rhus succedanea. *Phytochemistry* 1975A, 14, 1644–1647.

Chen, F.C.; Y.M.; Hung. J.G. Phenolic compounds from the heartwood of *Gracinia multiflora. Phytochemistry,* 1957B, 14, 300–303.

Cholbi, M.R.; Paya, M.; Alcaraz, M.J. Inhibitory effects of phenolic compounds on $CCl_4$ induced microsomal lipid peroxidation. *Experientia,* 1991, 47, 195–199.

Chou, T.–C.; Talalay, P. Quantitative analysis of dose–effect relationships: The combined effects of multiple drugs or enzyme inhibitors. *Adv. Enz. Regul.,* 1984, 22, 27–35.

Couch, R. B.; Jackson, G. G. Antiviral agents in influenza—Summary of influenza workshop VIII. *J. Infect. Dis.* 1976, 134, 516–527.

Degelau, J; Somani, S. K.; Cooper, S. L.; Guay, D. R. P.; Crossley, K. B. Amantadine–resistant influenza A in a nursing facility. *Arch. Intern. Med.* 1992, 152, 390–392.

Ono, K.; Nakane, H.; Jukushima, M.; Chermann, J.K.; Barre–Sinoussi, F. Inhibition of reverse transcriptase activity by a flavonoid compound, 5,6,7–trihydroxyflavone. *Biochem. Biophys. Res. Commu.,* 1989, 160, 982–987.

Dolin, R.; Reichman, R. C.; Madore, H. P.; Maynard, R.; Lindon, P. M.; Webber–Jones, J. A controlled trial of amantadine and rimandatine in the prophylaxis of influenza A infections. *N. Engl. J. Med.* 1982, 307, 580–584.

Doong, S. L.; Tsai, C. H.; Schinazi, R. F.; Liota, D. C.; Cheng, Y. C. Inhibition of the replication of hepatitis B virus in vitro by 2',3'–dideoxy–3'–thiacytidine and related analogues. *Pro. Natl. Acad. Sci. USA* 1991, 88, 8495–8499.

Gallo, R.C.; Salahuddin, S.Z.; Popovic, M.; Shearer, G.M.; Kaplan, M.; Haynes, B.F.; Palker, T.J.; Redfield, R.; Oleske, J.; Safai, B.; White, G.; Foster, P.; Markham, P.D. Frequent and detection and isolation of cytopathic retroviruses (HTLV–III) from patients with AIDS and at risk for AIDS. *Science,* 1984, 224, 500–503.

Geiger, H.; Seeger, T.; Hahn H.; Zinsmeister, H.D. 1H NMR Assignments in biflavanoid spectra by proton–detected C–H correlation. *Z. Naturforsch,* 1993, 48c, 821–826.

Hayashi, T.; Morita, N. Mechanism of action of the antiherpesvirus biflavone ginkgetin. *Antimicrob. Agents Chemother.,* 1992, 36, 1890–1893.

Hayden, F. G.; Belshe, R. B.; Clover, R. D.; Hay A. J.; Oakers, M. G.; Soo, W. Emergence and apparent transmission of rimantadine–resistant influenza virus in families. *N. Engl. J. Med.* 1989, 321, 1696–1702.

Hoffman, C. E. Amantadine HC1 and related compounds. In *Selective Inhibitors of Viral Functions;* Carte, W. A., Ed.; CRC Press: Cleveland, 1973, 199–211.

Hoffnagle, J. H. Chronic hepatitis B, *N. Engl. J. Med.* 1990, 323, 337–339.

Huang, L.; Kashiwade, Y.; Cosentino, L.M.; Fan, S.; Chen, C.H.; McPhail, A.T.; Fujoika, T.; Mihasha, K.; and Lee, K.H. Anti–AIDS Agents. 15. Synthesis and Anti–HIV Activity of Dihydroseselins and Related Analogs. *J. Med. Chem.,* 1994, 37, 3947–3955.

Iwu, M.M.; Igbokao, O.A.; Onwuchekwa, U.A; Okunii, C.O. Evaluation of the antihepatotoxic activity of the biflavonoids of Garcinia kola seed. *J. Ethnopharmacol.,* 1987, 21, 127–138.

Kimberlin, D. W.; Crampacker, C. S.; Straus, S. E.; Biron, K K.; Drew, W. L.; Hayden, F. G.; McKinlay, M.; Richman, D. D.; Whitley, R. J. Antiviral resistance to clinical practice. *Antiviral Res.,* 1995, 26, 423–438.

Knight, V.; Gilbert, B. E. Ribavirin aerosol treatment of influenza. In *Infectious Disease Clinics of North America,* vol. 1.; Moellering, Jr.. Ed.; 1987, 441–457.

Konoshima, T.; Takasaki, M.; Kozuka, M.; Lin, Y.M.; Chen, F.C.; Tokuda, H.; Matsumoto, T. Studies on inhibitors of skin tumors promotion (IV). Inhibitory effects of flavonoids on Epstein–Barr virus activation (1). *Shoyakugaku Zasshi,* 1988, 42, 343–346.

Korba, B.E.; Milman, G. A cell culture assay for compounds which inhibit hepatitis B virus replication. *Antiviral Res.,* 1991, 15, 217–228.

Korba, B.E.; Gerin, J.L. Use of a standardized cell culture assay to assess activities of nucleoside analogs against hepatitis B virus replication. *Antiviral Res.,* 1992, 19, 55–70.

Korba, B.E.; Gerin, J.L. Antisense oligonucleotides are effective inhibitors of hepatitis B virus replication in vitro. *Antiviral Res.,* 1995, 28, 225–242.

Li–zhen, X.; Chem, Z.; sun, N. Studies of Chemical Compositions of *Podocarpus nerifolius* D. Don. *Zhiwu Xuebao,* 1993, 35, 138–143 (English Abstract).

Lin, Y.M.; Chen. F.C. Robustaflavone from the seed–kernels of *Rhus succedanea. Phytochemistry,* 1974, 13, 1617–1619.

Lin, Y.M.; Chen, F.C. Agathisflavone from the drupes of *Rhus succedanea. Phytochemistry,* 1974B, 13, 657–658.

Lin, Y,M,; Chen. F.C.; Lee, K.H. Hinokiflavone, a cytotoxic principle from Rhus succdeanea and the cytoxicity of the related biflavonoids. *Planta Medica,* 1989, 55, 166–168.

Lopez–Saez, J.A.; Perez–Alonso, M.; Negueruela, A.V. Biflavanoids of *Selaginella denticulata* growing in Spain. *Z. Naturforsch.,* 1994, 49c, 267–270.

Magri, N.J.; Kinston, D.G.I. Modified Toxols, 4. Synthesis and biological activity of toxols modified in the side chain. *J. Nat. Prod.,* 1987, 51, 298–306.

Markham, K.R.; Sheppard, C.; Geiger, H. $^{13}C$ NMR studies of some naturally occurring amentoflavone and hinokiflavone biflavanoids. *Phytochemistry,* 1987, 26, 3335–3337.

Martin, P. and Friedman, L. S. In *Innovations in Antiviral Development and the Detection of Virus Infections;* T. M. Block; D. Junkind; R. L. Crowell; M. Dension; L. R. Walsh, Ed.; Plenum Press: New York, 1992, 111–120.

Mast, E. E.; Harmon, M. W.; Gravenstein, S.; Wu, S. P.; Arden, H. H.; Circo, R.; Tyszka, G.; Kenal, A. P.; Davis, J. P. Emergence and possible transmission of amantadine–resistant viruses during nursing home outbreaks of influenza A(H3N2). *Am J. Epidemiol.* 1992, 134, 988–997.

McDougal, J.S.; Cort, S.P.; Kennedy, M.S.; Cabridilla, C.D.; Feorino, P.M.; Francis, D.P.; Hicks, K.; Kalyanaramen, V.S.; Martin, L.S. Immunoassay for the detection and quantitation of infectious human retrovirus, lymphadenopathy–associated virus (LAV). *J. Immun. Meth.* 1985, 76, 171–183.

Mora, A.; Paya, M.; Roips, K. Structure–activity relationships of polymethoxyflavones and other flavonoids as inhibitor of non–enzymatic lipid peroxidation. *Biochem–Pharmacol.,* 1990, 40, 793–797.

Muller, C.; Bergmann, K.F.; Gerin, J.L.; Korba, B.E. Production of hepatitis B virus by stably transfected monocytic cell line U–937: a model for extrahepatic hepatitis B virus replication. *J. Infect. Dis.,* 1992, 165, 929–933.

Murakami, A.; Ohigashi, H.; Jisaka, M.; Irie, R.; Koshimizu, K. Inhibitory effects of new types of biflavonoid–related polyphenols; lophirone A and lophiraic acid, on some tumor promoter–induced biological responses in vitro and in vivo. *Cancer Lett.* (Shannon, Irel.), 1991, 58, 101–106.

Nagai, T.; Miyaichi, Y.; Tomimori, T.; Suzuki, Y.; Yamada, N. Inhibition of influenza virus sialidase and anti–influenza virus activity by plant flavonoids. *Chem. Pharm. Bull.,* 1990, 38, 1329–1332.

Nagai, T.; Miyaichi, Y.; Tomimore, T.; Suzuki, Y.; Yamada, H. In vivo anti–influenza virus activity of plant flavonoids possessing inhibitory activity for influenza virus sialidase. *Antiviral Res.,* 1990, 19:207–217.

Nagai, T.; Suzuki, Y.; Tomimore, T.; Yamada, H. Antiviral activity of plant flavonoid, 5,7,4'–trihydroxy–8–methoxyflavone, from roots of *Scutellaria baicalenais* against influenza A (H3N2) and B viruses. *Biol. Pharm. Bull.,* 1995, 18, 295–299.

Nagai, T.; Moriguchi, R.; Suzuki, Y.; Tomimori, T.; Yamada, H. Mode of action of the anti–influenza virus activity of plant flavonoid, 5,7,4'–trihydroxy–8–methoxyflavone, form the roots of *Scutellaria baicalensis. Antiviral Res.* 1995, 26, 11–25.

Nakazawa, K. Chemical structure of ginkgetin. Gifu Yakka Diagaku. Kiyo, 1941, 12, 1, *Chem. Abst.* 59, 2759d.

Ono, K.; Nakane, H.; Jukushima, M.; Chermann, J.K.; Barre–Sinlussi, F. Differential inhibitory effects of various flavonoids on the activities of reverse transcriptase and cellular DNA and RNA polymerases. *Euro. J. Biochem.,* 1990, 190, 469–476.

Qasim, M.A., Roy, S.K.; Ilyas, M. Phenolic Constituents of *Selaginellaceae. Indian Journal of Chemistry,* 1985, 24B, 220.

Ray, C. G.; Icenogle, T. B.; Minnich, L. L; Copeland, J. G.; Grogan, T. M. The use of intravenous ribavirin to treat influenza virus–associated acute myocarditis. *J. Infect Dis.,* 1989, 159, 829–836.

Sanz, M.J.; Ferrandiz, M.J.; Cejudo, M.; Terencia, M.C.; Gil, B.; Bustos, G.; Ubeda, A.; Gunasegaran, R.; Alcaraz, M.M. Influence of a series of natural flavonoids on free radical generating systems, and oxidative stress. *J. Xenobiotica,* 1994, 24, 689–699.

Schinazi, R.F.; Canno, D.L.; Arnold, B.H.; Martino–Saltzman, D. Combination of isoprinosine and 3'–azido–3'–deoxythymidine in lymphocytes infected with human immunodeficiency virus type 1. *Antimicrob. Agents Chemother.,* 1988, 32, 1784–1787.

Schinazi, R.F.; Sommadossi, J.P.; Saalman, V.; Cannan, M.W.; Hart, G.; Smith, G.; Hahn, E. Activity of 3'–azido–3'deoxythimidine nucleotide dimmers in primary lymphocytes infected with human immunodeficiency virus type 1. *Antimicrob. Agents Chemother.,* 1990, 34, 1061–1067.

Sidwell, R.W.; Bailey, D.W.; Wong, M.H.; Huffman, J.H.: In vitro and in vivo sensitivity of a non–mouse–adapted influenza (Bejing) virus infection to amantadine and ribavirin. *Chemotherapy,* 1995, 41, 455–461.

Sidwell, R.; Huffman, R.; Gilbert, B.; Moscon, G.; Pedersen, R.; Burger, R.,; Warren, R. Utilization of pulse oximetry for the study of the inhibitory effects of antiviral agents on influenza virus in mice. *Antimicrob. Ag. Chemother.,* 1992, 36, 473–476.

Silva, G.L.; Chai, H.; Gupta, M.P.; Farnsworth, N.R.; Cordell, G.A.; Pezzuto, J.M.; Beecher, C.W.W.; Kinghorn, A.D. Cytotoxic biflavanoids from *Selaginella willdenowii. Phytochemistry,* 1995, 40, 129–134.

Spira, T.J.; Bozeman, L.H.; Holman, R.C.; Warfield, K.T.; Phillips, S.K.; Feoprino, P.M. Micromethod for assaying the reverse transcriptase of LAV–HTIV–III/lymphadenopathy–associated virus. *J. Clin. Microbiol.,* 1987, 25, 97–99.

Tan, G.T.; Pezzuto, J.M.; Kinghorn, A.D. Evaluation of natural products as inhibitors of human immunodeficiency virus type 1 (HIV–1) reverse transcriptase. *J. Nat. Prod.,* 1991, 54, 143–154.

Tisdale, M.; Bauer, D. J. The relative potencies of anti–influenza compounds. *Ann. N. Y. Acad. Sci.* 1977, 284, 254–263.

Tsunoda, A.; Maasab, H. H.; Cochran, K. W.; Eveland, W. C. Antiviral activity of $\alpha$–methyl–1–adamantane methylamine hydrochloride. *In Antimicrob. Agents Chemother.* 1966, 553.

van Leeuwen R.; Katlama, C.; Kitchen, V.; Boucher, C. A. B.; Tubiana, R.; McBride, M.; Ingrand, D.; Weber, J.; Hill, A.; McDade, H.; Damer S. A. Evaluation of safety and efficacy of 3TC (Lamivudine) in patients with asymptomatic or mildly symptomatic human immunodeficiency virus infection: A phase I/II study. *J. Inf. Dis.* 1995, 171, 1166–1171.

Yokoshuka, O.; Omata, O. M.; Imazeki, F.; Okauda, K.; Summers, J. Changes of hepatitis B virus DNA in liver and serum caused by recombinant leukocyte interferon treatment: analysis of intrahepatic replicative hepatitis B virus DNA. *Hepatology* 1985, 5, 728–734.

Chen, et al., "Rhusflavanone, a New Biflavanone from the Seeds of Wax–tree," *J. of The Chemical Society,* pp. 98–101 (1976).

Ezio, "Topical administration of plant extracts having therapeutic activities for treatment of fat deposits," *Chem. Abst.,* vol. 115, Abst. No. 189759m (1991).

Fujita, et al., "Nucleic acid determination by phosphatase––labeled DNA probe using fluorescent coumarin compounds as the enzyme substrate," *Chem. Abst.,* vol. 115, Abst. No. 251633w (1991).

Kadono, et al., "Antiviral powder, antiviral extract, and pharmaceutical preparation containing said powder and/or said extract," *Chem. Abst.,* vol. 123, Abst. No. 208781w (1995).

Kozuka, et al., "Hinokiflavone and kayaflavone as antiviral agents," *Chem. Abst.,* vol. 113, Abst. No. 46254r (1989).

Lamer–Zarawska, et al., "Chemical and taxonomic studies on some species from the Juniperus L. Genus," *Chem. Abst.,* vol. 100, Abst. No. 117812r (1983).

MAPE Establishment Ger. Offen. DE 3,544,457, "Garcinikolin, a biflavanoid from Garcinia kola, for treatment of liver disease," Chem. Abst., vol. 107, Abst. No. 211872b (1987).

Spedding, et al., "Inhibition of reverse transcriptases by flavonoids," Antiviral Research, vol. 12, pp. 99–110 (1989).

Tokuda, et al., "Bilobetin as virus genome inactivating agent," Chem. Abst., vol. 112, Abst. No. 16256e (1989).

Wleklik, et al., "Interferon–inducing activity of flavonoids," Chem. Abst., vol. 107, Abst. No. 1267026 (1987).

Wleklik, et al., "Structural basis for antiviral activity of flavonoids—naturally occurring compounds," Chem. Abst., vol. 111, Abst. No. 173 u (1988).

Bernstein, et al., "Chemotherapy of Experimental Tuberculosis," The American Review of Tuberculosis, vol. 65, No. 4, pp. 357–364 (1952) U.S.

Fa–Ching Chen, et al., "Phenolic compounds from the heartwood of garcinia multifolora," Phytochemistry, vol. 14, pp. 300–303 (1975) England.

Fa–Ching Chen, et al., "Synthesis of Hexa–O–Methyl–8, 8"–Binaringenin," Heterocycles, vol. 3, No. 10, pp. 833–835 (1975).

Fa–Ching Chen, et al., "Synthesis of 7–Halogenoflavone and Related Compounds," J. Chem. Soc., pp. 146–150 (1958).

Fa–Ching Chen, et al., "Synthesis of Halogenoflavonoids VIII. Synthesis of 6–Halogenoflavones and Related Compounds," J. Formosan Sci., vol. 8, pp. 74–75 (1954).

Fa–Ching Chen, et al., "Synthesis of 6–Halogenoflavonoids and Related Compounds," J. Chem. Soc., pp. 3414–3417 (1961).

Fa–Ching Chen, et al., "Synthesis of Halogenoflavonoids VII. Synthesis of 2–, 3–, and 4– Fluoro–2'–Oxychalcone," J. Formosan Sci., vol. 8, pp. 71–73 (1954) Taiwan.

Collins, et al., "Microplate Alamar Blue Assay versus BACTEC 460 System for High–Throughput Screening of Compounds agains Mycobacterium tuberculosis and Mycobacterium avium," Antimicrob. Agents and Chemother., vol. 41, No. 5, pp. 1004–1009 (1997) U.S.

H. Herbert Fox, "The Chemical Approach to the Control of Tuberculosis," Science, vol. 116, pp. 129–134 (1952) U.S.

Inderlied, et al., "Antimicrobial Agents and Susceptibility Tests: Mycobacteria," Manual of Clinical Microbiology, 6$^{th}$ Ed., pp. 1385–1404 (1995) U.S.

Ariyan, et al., "Heterocyclic Compounds of Chalcone Type," J. Chem. Soc., pp. 2242–2244 (1961).

Fa–Ching Chen, et al., "Succedaneaflavanone—A New 6,6'–Binaringenin from RHUS Succedanea*," Phytochemistry, vol. 14, pp. 1644–1647 (1975) England.

Fa–Ching Chen, et al., "Rhusflavanone, a New Biflavanone from the Seeds of Wax–tree," J. Chem. Soc., pp. 98–101 (1976).

Fa–Ching Chen, et al., "Synthesis of Biflavonyls," Proc. Chem. Soc., pp. 232–240 (1959).

Inderlied, et al, "Antimycobacterial Agents: In Vitro Susceptibility Testing, Spectra of Activity, Mechanisms of Action and Ressistance, and Assays for Activity in Biologic Fluids," Antibiotics in Laboratory Medicine, 4$^{th}$ Ed., pp. 127–175 (1996) U.S.

Kohler, et al., "Benzalacetophenone," Organic Synthesis, vol. 2, No. 1, pp. 1–2 (1922).

Yuh–Meei Lin, et al., "Agathisflavone from the drupes of RHUS Succedanea," Phytochemistry, vol. 13, pp. 657–658 (1974) England.

Yuh–Meei Lin, et al., "Robustaflavone from the seed–kernels of THUS Succedanea," Phytochemistry, vol. 13, pp. 1617–1619 (1974) England.

D.A. Mitchison, "The Garrod Lecture: Understanding the chemotherapy of tuberculosis—current problems," J. of Antimicrobial Chemotherapy, vol. 29, pp. 477–493 (1992) Britain.

Nivin, et al., "A Continuing Outbreak of Multidrug–Resistant Tuberculosis, with Transmission in a Hospital Nursery," Clin. Infect. Dis., vol. 26, pp. 303–307 (1988) U.S.

F.N. Ozdemir, et al., "Tuberculosis Remains an Important Factor in the Morbidity and Mortality of Hemodialysis Patients," Transplantation Proceedings, vol. 30, pp. 846–847 (1998) U.S.

Pablos–Mendez, et al., "Global Surveillance for Antituberculosis–drug Resistance," The New England Journal of Medicine, vol. 338, No. 23, pp. 1641–1649 (1998) U.S.

Pansy, et al., "In Vitro Studies on Isonicotinic Acid Hydrazine," AM. Rev. Tuberc., vol. 65, pp. 761–764 (1952).

A. Peterson, "FDA Approves the First New Treatment for Tuberculosis in More Than Decade," Wall Street Journal, pp. B5 (1998) U.S.

Raviglione, et al., "Global Epidemiology of Tuberculosis," JAMA, vol. 273, No. 3, pp. 220–222 (1995) U.S.

Robitzek, et al., "Hydrazine Derivatives of Isonicotinic Acid (Rimifon$^1$, Marsilid$^2$) in the Treatment of Active Progressive Caseous–Pneumonic Tuberculosis," Am. Rev. Tuberc., vol. 65, pp. 402–428 (1952).

Siddiqi, "Radiometric (BACTEC) Tests for Slowly Growing Mycobacteria," American Society for Microbiology, pp. 5.14.2–5.14.25 (1992).

Ben–Hur, et al., "Vitamin E and derivatives for prevention of damage in red cells sterilized by phthalocyanines and light," Chemical Abstracts, vol. 123, pp. 680 (208776y).

Beretz, et al., "Inhibition of 3', 5+–AMP phosphodiesterase by biflavonoids and xanthones," 7–Enzymes, vol. 91, No. 1991, pp. 153422 (153416u).

Hayashi, et al., "Mechanism of action of the antiherpesvirus biflavone ginkgetin," 1–Pharmatology, vol. 117, pp. 225798, 1991 (225973v).

Ishitsuka, et al., "Antipicornavirus Flavone Ro 09–0179," Antimicrobioal Agents and Chemotherapy, vol. 22, No. 4, pp. 611–616, 1982.

Kurokawa, et al., "Efficacy of traditional herbal medicines in combination with acyclovir against herpes simplex virus type 1 infection in vitro and in vivo," Chemical Abstracts, vol. 123, pp. 34, 1995 (334v).

Kurokawa, et al., "Effects of traditional herbal medicines against herpes simplex virus (HSV) type 2 and acyclovir—resistant HSV type 1 in vitro and in vivo," Chemical Abstrcts, vol. 124, No. 21, 1996, (124:278137k).

Lin, et al., "Medicinal Plants Used for the Treatment of Hepatitis in Taiwan," American J. of Chinese Medicine, vol. 18, Nos. 1–2, pp. 35–43, 1990.

Lin, et al., "Antitumor agents. CII. Hinokiflavone, a cytotoxic principle from Rhus succedanea and the cytotoxicity of the related biflavonoids," 1–Pharmacology, vol. 111, pp. 70319, 1989 (70319v).

Mucsi, et al., "Combined Effects of Flavonoids and Acyclovir Against Herpesviruses in Cell Cultures," Acta Microbiologica Hungarica, vol. 39, No. 2, pp. 137–147, 1992.

Mucsi, et al., "Inhibition of virus multiplication and alteration of cyclic AMP level and cell cultures by flavonoids," Experientia, vol. 41, pp. 930–931, 1985.

Reischle, et al., "Homeopathic remedies for treatment of damage to the immune system," 63–Phamaceuticals, vol. 122, pp. 64320, 1995 (64310w).

Wleklilk et al., "Interferon—Inducing Activity of Flavonoids," *ACTA Microbiologica Polonica,* vol. 36, No. ½, 1987.

Yukawa, et al., "Prophylactic treatment of cytomegalovirus infection with traditional herbs," *Chemical Abstracts 1–Pharmacology,* vol. 125, pp. 265067, 1996 (265061b).

* cited by examiner

BETA-FLUOROETHYL THIOUREA COMPOUNDS AND USE

This application is a continuation-in-part of provisional application Ser. No. 60/155,519, filed Sep. 22, 1999.

FIELD OF THE INVENTION

The present invention relates to methods and compositions for preventing or treating mycobacterium infections, particularly tuberculosis infections.

BACKGROUND OF THE INVENTION

Infectious diseases remain the largest cause of death in the world today, greater than cardiovascular disease or cancer.[1] Among infectious diseases, tuberculosis (TB) is the leading cause of death.[2]

Tuberculosis, caused by the infection of *Mycobacterium tuberculosis* (Mtb), kills three million people worldwide and eight million people develop the disease each year according to current estimates by the World Health Organization (WHO). More people die from TB than from malaria, diarrhea, AIDS and tropical diseases combined.

Tuberculosis mainly affects the lungs but can also involve other organs. TB strikes people of all ages, but is more common among the elderly. The disease can also afflict animals, especially livestock such as cattle, hogs and poultry. This disease once ranked among the most common causes of death in the world. Today, improved methods of prevention, detection, diagnosis and treatment have greatly reduced both the number of people who contract the disease and the number of people who die from it. However, in the last decade, the outbreaks of multidrug-resistant tuberculosis (MDRTB) and TB amplified by the global HIV pandemic make TB an urgent global issue.

One third of the world's population is infected with Mtb,[3] a facultative intracellular bacillus. After infection with Mtb, the lifetime risk of developing TB is approximately 10%, while 90% of infected persons have latent infection with viable bacilli. This 10% rate of TB accounts for the 8 million persons reported annually with active TB, and the resultant 3 million deaths. Moreover, TB is a serious problem faced by hemodialysis patients,[4] and is the number one killer of women of childbearing age around the world, with 1.2 million women dying of the disease in 1997, according to reports by the WHO.[5]

TB infection is a serious problem for acquired immunodeficiency syndrome (AIDS) patients. HIV-infected individuals are particularly susceptible to infection with Mtb and the development of TB. Compared to an individual who is not infected with HIV, an individual infected with HIV has a 10 times greater risk of developing TB. In an individual infected with HIV, the presence of other infections, including TB, may allow HIV to multiply more quickly. This may result in more rapid progression of HIV infection and AIDS.[6] As HIV infection progresses, CD4+ lymphocytes decline in number and function. The immune system is less able to prevent the growth and local spread of Mtb. Even in HIV-infected patients, pulmonary TB (PTB) is still the most common form of TB. The presentation of the disease depends on the degree of immunosuppression. As in adults, the natural history of TB in a child infected with HIV depends on the stage of HIV disease. Early in HIV infection, when immunity is strong, the signs of TB are similar to those in a child without HIV infection. As HIV infection progresses and immunity declines, dissemination of TB becomes more common and tuberculous meningitis, miliary tuberculosis, and widespread tuberculous lymphadenopathy occur more frequently.

HIV-positive patients and staff in health units face daily exposure to TB. The risk of exposure is greatest in adult medical wards and TB wards where there are many PTB cases. From 1990–1992, the Centers for Disease Control (CDC) investigated outbreaks of MDRTB in several hospitals and a state correctional system. Almost 300 cases of MDRTB were identified in these outbreaks; most patients were HIV-seropositive. The mortality rate was 80%–90% and the median interval from diagnosis of tuberculosis to death ranged from 4–16 weeks.[7] In 1995, about one third of the 17 million HIV-infected people worldwide were also co-infected with Mtb.[6]

Current treatment of TB requires taking at least two antibiotics, usually isoniazid and rifampicin, supplemented with pyrazinamide and ethambutol added when isoniazid resistance is suspected.

Isoniazid (isonicotinic acid hydrazide) (INH) was first reported to be effective against Mtb and *M. bovis* in 1952.[8-10] Isoniazid, now still a front-line therapy against TB, has been shown to be an effective prophylactic antitubercular[11], and modern short-course chemotherapy is initiated with three drugs: isoniazid, rifampin and pyrazinamide (PZA), often with the inclusion of a fourth drug, usually ethambutol. Recently, rifapentine, a derivative of rifamycin, was approved by the FDA for the treatment of tuberculosis.[12]

The American Thoracic Society and the CDC in the United States now recommend a treatment regimen of isoniazid, rifampin and pyrazinamide for 2 months, followed by isoniazid and rifampin for an additional 4 months, as the standard 6-month regimen. Isoniazid, cheap and safe, has a wide therapeutic margin and high early bactericidal activity so that it kills rapidly growing bacilli in lesions, but is inefficient in ultimately sterilizing these lesions. Rifampin and PZA are crucial in achieving sterilization by killing persisting semi-dormant bacilli, and are thus responsible for shortening the duration of treatment from the earlier norm of 12–18 months to the current standard of 6 months.[13] However, many people fail to complete the lengthy therapy, treatment failures are high and MDR is increasing. A four-year study, led by the WHO, shows that of people who had been treated for TB for less than a month, 36 percent harbored microbes that resisted at least one of the four main anti-tuberculosis drugs. Moreover, 10% of infected people who had never been treated for the disease carried a strain of Mtb that resisted at least one drug.[14]

Drug resistance resulting from inadequate treatment, such as irregular drug supply, inappropriate regimens or poor compliance is a potential threat to TB control programs throughout the world. Patients infected with strains resistant to multiple drugs are less likely to be cured, particularly if they are infected with HIV or malnourished, and their treatment is more toxic and more expensive than the treatment of patients with susceptible organisms.

The resurgence of TB, the development of MDR to Mtb and the discovery that the progression of TB is accelerated in HIV-positive patients have intensified the need to develop more efficient drugs to combat this disease.

BRIEF SUMMARY OF THE INVENTION

The present invention relates to compounds, compositions and methods for treating and/or preventing mycobacterium infections, especially tuberculosis infections, in patients. The method is useful for treating or preventing mycobacterium infections in immunocomprised patients, particularly HIV infected patients.

The present invention relates to compounds, compositions and methods for the prevention or treatment of mycobacterium infections. The compounds are naturally occurring and synthetic biflavonoids, flavonoids, chalcones and chalcone like compounds. The compounds were screened for anti-mycobacterium activity and several were found to cause inhibition of a mycobacterium infection. Of these, eight were identified as particularly potent, exhibiting greater than 90% inhibition of the growth of Mtb at a concentration of 12.5 μg/mL. The actual minimum inhibitory concentrations (MIC), defined as the lowest concentration inhibiting 99% of the inoculum, for the preferred compounds ranged from 6.8 to 48.3 μM.

Accordingly, one object of the invention is a method for preventing or treating a mycobacterium infection in a mammal comprising administering to a mammal in need of anti-mycobacterium prevention or treatment an effective anti-mycobacterium amount of at least one compound of formula i.

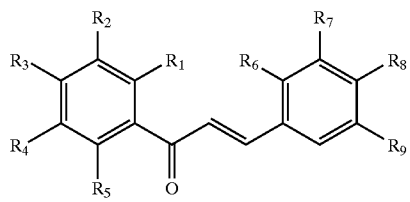

i wherein $R_1$–$R_9$ are independently comprised of H; $OCH_3$; EtO; OH; O-alkenyl; phenyl; $NH_2$; COOH; F; Cl; Br; I; $CONH_2$; $NO_2$; $NR_{10}R_{11}$ $OCONR_{10}R_{11}$ wherein $R_{10}$ and $R_{11}$ independently comprise H alkyl (e.g., $C_{1-6}$ linear or branched alkyl) or aryl (e.g., unsubstituted phenyl or phenyl substituted with one or more of the following: $C_{1-6}$ alkyl, $C_{1-6}$ alkoxy, hydroxy-C1–4 alkyl, hydroxyl, amino, $C_{1-6}$ alkylamino, di($C_{1-6}$ alkyl)amino, amino-$C_{1-8}$ alkyl, $C_{1-8}$ alkylamino-$C_{1-8}$ alkyl, di($C_{1-6}$ alkyl)amino-$C_{1-8}$ alkyl, nitro, azido or halogen); $COR_{12}$ wherein $R_{12}$ comprises H, OH, O-alkyl (e.g., $C_{1-6}$ linear or branched alkyl), O-aryl (e.g., unsubstituted phenyl or phenyl substituted with one or more of the following: $C_{1-6}$ alkyl, $C_{1-6}$ alkoxy, hydroxy-C1–4 alkyl, hydroxyl, amino, $C_{1-6}$ alkylamino, di($C_{1-6}$ alkyl) amino, amino-$C_{1-8}$ alkyl, $C_{1-8}$ alkylamino-$C_{1-8}$ alkyl, di($C_{1-6}$ alkyl)amino-$C_{1-8}$ alkyl, nitro, azido or halogen) or amino; $NHCOCH_3$; $O_2^-$; $OCOR_{13}$ wherein $R_{13}$ comprises alkyl (e.g., $C_{1-6}$ linear or branched alkyl) or aryl (e.g., unsubstituted phenyl or phenyl substituted with one or more of the following: $C_{1-6}$ alkyl, $C_{1-6}$ alkoxy, hydroxy-C1–4 alkyl, hydroxyl, amino, $C_{1-6}$ alkylamino, di($C_{1-6}$ alkyl) amino, amino-$C_{1-8}$ alkyl, $C_{1-8}$ alkylamino-$C_{1-8}$ alkyl, di($C_{1-6}$ alkyl)amino-$C_{1-8}$ alkyl, nitro, azido or halogen); OAc; benzoyl; $CONH_2$; or $NO_2$; or a pharmaceutically acceptable derivative or salt thereof.

Compounds of the formula i as well as anti-mycobacterium compositions comprising compounds of the formula i are included within this aspect of the invention.

Another object of the invention is a method for preventing or treating a mycobacterium infection in a mammal comprising administering to a mammal in need of anti-mycobacterium prevention or treatment an effective anti-mycobacterium amount of at least one compound of formula ii.

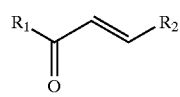

ii wherein $R_1$ comprises 4-fluorophenyl-, 3-hydroxyphenyl-, pyridin-3-yl-, furan-2yl-, phenanthren-2-yl-, 3-fluorenyl-, pyridin-2-yl-, naphthalen-1-yl-, pyridin-2-yl-, 4-bromo-2-hydroxyphenyl-, pyridin-4-yl-, 2-hydroxy-4-methoxyphenyl-, 4-aminophenyl-, pyridin-4-yl-, 2-hydroxy-5-methoxyphenyl-, 4-methoxyphenyl-, 4-methoxyphenyl-, 2-hydroxy-5-chlorophenyl-, 4-aminophenyl-, 3-hydroxynaphthalen-2-yl-, furan-2-yl- or pyridin-2-yl-; and $R_2$ comprises pyridin-3-yl-, phenanthren-9-yl-, phenanthren-9-yl-, phenyl-, 2-aminopyridino-3-yl, 2-aminopyridino-3-yl-, pyridin-2-yl-, phenyl-, 4-dimethylaminophenyl-, furan-2-yl-, indol-2-yl-, furan-2-yl-, 2-aminopyridin-3-yl-, 4-dimethylaminophenyl-, furan-2-yl-, pyridin-4-yl-, pyridin-3-yl-, 2-aminopyridin-3-yl-, 2-aminopyridin-3-yl-, pyridin-3-yl-, 2-aminopyridin-3-yl-, pyridin-4-yl- or 4-methoxyphenyl-; or a pharmaceutically acceptable derivative or salt thereof.

Compounds of the formula ii as well as anti-mycobacterium compositions comprising compounds of the formula ii are included within this aspect of the invention.

Another object of the invention is a method for preventing or treating a mycobacterium infection in a mammal comprising administering to a mammal in need of anti-mycobacterium prevention or treatment an effective anti-mycobacterium amount of at least one compound of formula iii.

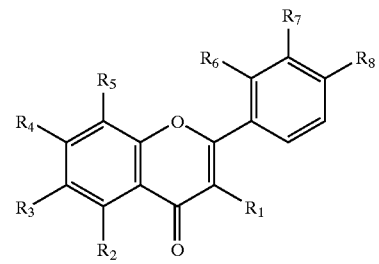

iii wherein $R_1$–$R_8$ are independently comprised of H; $OCH_3$; EtO; OH; O-alkenyl; sdphenyl; $NH_2$; COOH; F; Cl; Br; I; $CONH_2$; $NO_2$; $NR_{10}R_{11}$ $OCONR_{10}OR_{11}$ wherein $R_{10}$ and $R_{11}$ independently comprise H alkyl (e.g., $C_{1-6}$ linear or branched alkyl) or aryl (e.g., unsubstituted phenyl or phenyl substituted with one or more of the following: $C_{1-6}$ alkyl, $C_{1-6}$ alkoxy, hydroxy-C1–4 alkyl, hydroxyl, amino, $C_{1-6}$ alkylamino, di($C_{1-6}$ alkyl)amino, amino-$C_{1-8}$ alkyl, $C_{1-8}$ alkylamino-$C_{1-8}$ alkyl, di($C_{1-6}$ alkyl)amino-$C_{1-8}$ alkyl, nitro, azido or halogen); $COR_{12}$ wherein $R_{12}$ comprises H, OH, O-alkyl (e.g., $C_{1-6}$ linear or branched alkyl), O-aryl (e.g., unsubstituted phenyl or phenyl substituted with one or more of the following: $C_{1-6}$ alkyl, $C_{1-6}$ alkoxy, hydroxy-C1–4 alkyl, hydroxyl, amino, $C_{1-6}$ alkylamino, di($C_{1-6}$ alkyl) amino, amino-$C_{1-8}$ alkyl, $C_{1-8}$ alkylamino-$C_{1-8}$ alkyl, di($C_{1-6}$ alkyl)amino-$C_{1-8}$ alkyl, nitro, azido or halogen) or amino; $NHCOCH_3$; $O_2^-$; $OCOR_{13}$ wherein $R_{13}$ comprises alkyl (e.g., $C_{1-6}$ linear or branched alkyl) or aryl (e.g., unsubstituted phenyl or phenyl substituted with one or more of the following: $C_{1-6}$ alkyl, $C_{1-6}$ alkoxy, hydroxy-C1–4 alkyl, hydroxyl, amino, $C_{1-6}$ alkylamino, di($C_{1-6}$ alkyl) amino, amino-$C_{1-8}$ alkyl, $C_{1-8}$ alkylamino-$C_{1-8}$ alkyl, di($C_{1-6}$ alkyl)amino-$C_{1-8}$ alkyl, nitro, azido or halogen); OAc; benzoyl; $CONH_2$; or $NO_2$; or pharmaceutically acceptable derivative or salt thereof.

Compounds of the formula iii as well as anti-mycobacterium compositions comprising compounds of the formula iii are included within this aspect of the invention.

Another object of the invention is a method for preventing or treating a mycobacterium infection in a mammal comprising administering to a mammal in need of anti-mycobacterium prevention or treatment an effective anti-mycobacterium amount of at least one compound of formula iv.

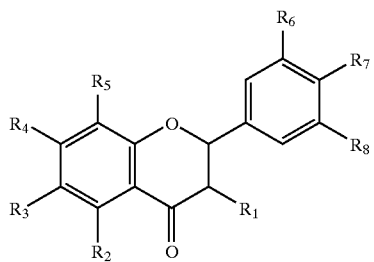

iv wherein $R_1$–$R_8$ are independently comprised of H; $OCH_3$; EtO; OH; O-alkenyl; phenyl; $NH_2$; COOH; F; Cl; Br; I; $CONH_2$; $NO_2$; $NR_{10}R_{11}$ $OCONR_{10}R_{11}$ wherein $R_{10}$ and $R_{11}$ independently comprise H alkyl (e.g., $C_{1-6}$ linear or branched alkyl) or aryl (e.g., unsubstituted phenyl or phenyl substituted with one or more of the following: $C_{1-6}$ alkyl, $C_{1-6}$ alkoxy, hydroxy-C1–4 alkyl, hydroxyl, amino, $C_{1-6}$ alkylamino, di($C_{1-6}$ alkyl)amino, amino-$C_{1-8}$ alkyl, $C_{1-8}$ alkylamino-$C_{1-8}$ alkyl, di($C_{1-6}$ alkyl)amino-$C_{1-8}$ alkyl, nitro, azido or halogen); $COR_{12}$ wherein $R_{12}$ comprises H, OH, O-alkyl (e.g., $C_{1-6}$ linear or branched alkyl), O-aryl (e.g., unsubstituted phenyl or phenyl substituted with one or more of the following: $C_{1-6}$ alkyl, $C_{1-6}$ alkoxy, hydroxy-C1–4 alkyl, hydroxyl, amino, $C_{1-6}$ alkylamino, di($C_{1-6}$ alkyl) amino, amino-$C_{1-8}$ alkyl, $C_{1-8}$ alkylamino-$C_{1-8}$ alkyl, di($C_{1-6}$ alkyl)amino-$C_{1-8}$ alkyl, nitro, azido or halogen) or amino; $NHCOCH_3$; $O_2^-$; $OCOR_{13}$ wherein $R_{13}$ comprises alkyl (e.g., $C_{1-6}$ linear or branched alkyl) or aryl (e.g., unsubstituted phenyl or phenyl substituted with one or more of the following: $C_{1-6}$ alkyl, $C_{1-6}$ alkoxy, hydroxy-C1–4 alkyl, hydroxyl, amino, $C_{1-6}$ alkylamino, di($C_{1-6}$ alkyl) amino, amino-$C_{1-8}$ alkyl, $C_{1-8}$ alkylamino-$C_{1-8}$ alkyl, di($C_{1-6}$ alkyl)amino-$C_{1-8}$ alkyl, nitro, azido or halogen); OAc; benzoyl; $CONH_2$; or $NO_2$; or pharmaceutically acceptable derivative or salt thereof.

Compounds of the formula iv as well as anti-mycobacterium compositions comprising compounds of the formula iv are included within this aspect of the invention.

Yet another object of the invention is a method for treating or preventing mycobacterium infection in a patient comprising biflavonoid compounds, particularly 6-6"-biapigenin hexamethylether, volkensiflavone hexamethylether, GB-1a hexamethylether, 3'''-Nitro-C3-O-C4'''-biflavone, 3'-8"-biflavone, 6-2'''-biflavone, 6-6"-binaringenin hexamethylether or 6-2'''-biapigenin or derivative or salt thereof and pharmaceutically acceptable carriers therefor.

Still yet another object of the invention is to provide anti-mycobacterium composition comprising biflavonoid compounds for treating or preventing a mycobacterium infection in a patient particularly 6-6"-biagpigenin hexamethylether, volkensiflavone hexamethylether, GB-1a hexamethylether, 3'''-Nitro-C3-O-C4'''-biflavone, 3'-8"-biflavone, 6-2'''-biflavone, 6-6"-binaringenin hexamethylether or 6-2'''-biapigenin or derivative or salt thereof and pharmaceutically acceptable carriers therefor.

These and other objects of the invention will be clear in light of the detailed description below.

DETAILED DESCRIPTION OF THE INVENTION

This invention relates to compounds, compositions and methods for treating or preventing mycobacterium infections in mammals. The compounds of the present invention are synthetic or naturally occurring chalcones, chalcone-like compounds, biflavonoids and flavonoids. The compounds were screened for anti-mycobacterium activity. Of the compounds showing anti-mycobacterium activity, eight were identified as particularly potent, exhibiting greater than 90% inhibition of the growth of Mtb at a concentration of 12.5 µg/mL.

The preferred compounds of this invention, which exhibited greater than 90% inhibition of the growth Mtb at a concentration of 12.5 µg/mL, were chalcone-like compounds (heterocyclic ring substituted 2-propen-1-one) 1-(4-fluorophenyl)-3-(pyridin-3-yl)-2-propen-1-one (53) (98%), 1-(3-hydroxyphenyl)-3-phenanthren-9-yl-2-propen-one (54) (97%), 1-(5-pyridin-2-yl)-3-(phenanthen-9-yl)-2-propen-1-one (55) (96) and 1-(furan-2-yl)-3-phenyl-2-propen- 1-one (56) (96%); chalcones 1-(2-hydroxyphenyl)-3-(3-chlorophenyl)-2-propen-1-one (24) (90%) and 1-(2-hydroxyphenyl)-3-(3-iodophenyl)-2-propen-1-one (40) (92%); and biflavonoids 6-6"-biapigenin hexamethylether (151) (96%), and volkensiflavone hexamethylether (3-8"-naringenylapigenin hexamethylether) (152) (95%). The actual minimum inhibitory concentrations (MIC), defined as the lowest concentration inhibiting 99% of the inoculum, for 53, 54, 55, 56, 24, 40, and 151 were 6.8, 19.2, 20.2, 31.5, 48.3, >35.7 and >20.1 µM, respectively. See Tables 1–5.

The compounds and compositions of the present invention can be used to treat or prevent mycobacterium infections. Representative mycobacterial organisms include *Mycobacterium aviurn* complex (MAC), *Mycobacterium kansaii*, *Mycobacterium marinum*, *Mycobacterium phlei*, *Mycobacterium ulcerans*, *Mycobacterium xenopi*, *Mycobacterium gordonae*, *Mycobacterium terrae* complex, *Mycobacterium haemophilum*, *Mycobacterium fortuitum*, *Mycobacterium tuberculosis*, *Mycobacterium laprae*, *Mycobacterium scrofulaceum* and *Mycobacterium smegmatis*. In practicing this invention, the compounds and compositions are particularly useful in treating *Mycobacterium tuberculosis* infections.

The compounds of the invention may be formulated as a solution of lyophilized powders for parenteral administration. Powders may be reconstituted by addition of a suitable diluent or other pharmaceutically acceptable carrier prior to use. The liquid formulation is generally a buffered, isotonic, aqeuous solution. Examples of suitable diluents are normal isotonic saline solution, standard 5% dextrose in water or in buffered sodium or ammonium acetate solution. Such formulation is especially suitable for parenteral administration, but may also be used for oral administration. It may be desirable to add excipients such as polyvinylpyrrolidone, gelatin, hydroxy cellulose, acacia, polyethylene glycol, mannitol, sodium choride or sodium citrate.

Alternatively, the compounds of the present invention may be encapsulated, tableted or prepared in an emulsion (oil-in-water or water-in-oil) syrup for oral administration. Pharmaceutically acceptable solids or liquid carriers, which are generally known in the pharmaceutical formulary arts, may be added to enhance or stabilize the composition, or to facilitate preparation of the composition. Solid carriers include starch (corn or potato), lactose, calcium sulfate dihydrate, terra alba, croscarmellose sodium, magnesium stearate or stearic acid, talc, pectin, acacia, agar, gelatin, maltodextrins and microcrystalline cellulose, or colloidal silicon dioxide. Liquid carriers include syrup, peanut oil, olive oil, corn oil, sesame oil, saline and water. The carrier may also include a sustained release material such as glyceryl monostearate or glyceryl distearate, alone or with a wax. The amount of solid carrier varies but, preferably, will be between about 10 mg to about 1 g per dosage unit.

The dosage ranges for administration of the compounds of the invention are those necessary to produce the desired affect whereby symptoms of infection are ameliorated. For example, as used herein, an anti-mycobacterium effective amount for treating or preventing a mycobacterium infection refers to the amount administered so as to maintain an amount which suppresses or inhibits mycobacterium infection as evidenced by standard assay. The dosage will also be determined by the existence of any adverse side effects that may accompany the compounds. It is always desirable, whenever possible, to keep adverse side effects to a minimum.

One skilled in the art can easily determine the appropriate dosage, schedule, and method of administration for the exact formulation of the composition being used in order to achieve the desired effective concentration in the individual patient. However, the dosage can vary from between about 0.001 mg/kg/day to about 50 mg/kg/day, but preferably between about 0.01 to about 1.0 mg/kg/day.

The following examples are illustrative of the invention but does not serve to limit its scope.

Experimental

General Experimental Procedures

Melting points were determined in open glass capillary tubes and are uncorrected. $^1$H-NMR and $^{13}$C-NMR spectra were recorded on a Varian XL300 NMR spectrometer in $CDCl_3$, $DMSO-d_6$ or acetone-$d_6$ as specified using TMS as an internal standard. Chemical shifts are expressed in parts per million (δ, ppm). IR spectra were recorded using a Midac FT-IR spectrometer, with samples being prepared as KBr pellets, or using a Perkin-Elmer spectrum 1000 FT-IR. Mass spectral data were recorded using a Finnegan MAT 90 mass spectrometer. Analytical thin-layer chromatography (TLC) was carried out on precoated plates (silica gel $F_{254}$ from EM Science). Column chromatography was performed with silica gel 60 (70–230 mesh from EM Science). The structures of compounds were confirmed by their TLC profiles as well as their IR, NMR and MS spectra.

EXAMPLE 1

Chalcones (1,3-Diaryl-2-propen-1-ones) and Chalcone-Like Compounds (1,3-Diheterocyclic ring substituted 2-Propen-1-ones): Chalcones and chalcone-like compounds were prepared by base-catalyzed condensation of appropriately substituted ketones with substituted benzaldehydes or heterocylic aldehydes (Scheme 1). To the mixture of the substituted acetophenone and substituted benzaldehyde in alcohol was added a 60% solution of potassium hydroxide dropwise with stirring. The reaction mixture was kept at 0° C. for 2 days, then diluted with water and acidified with acetic acid. The precipitated chalcone was collected and recrystalized from alcohol to yield pure chalcone.[15,16]

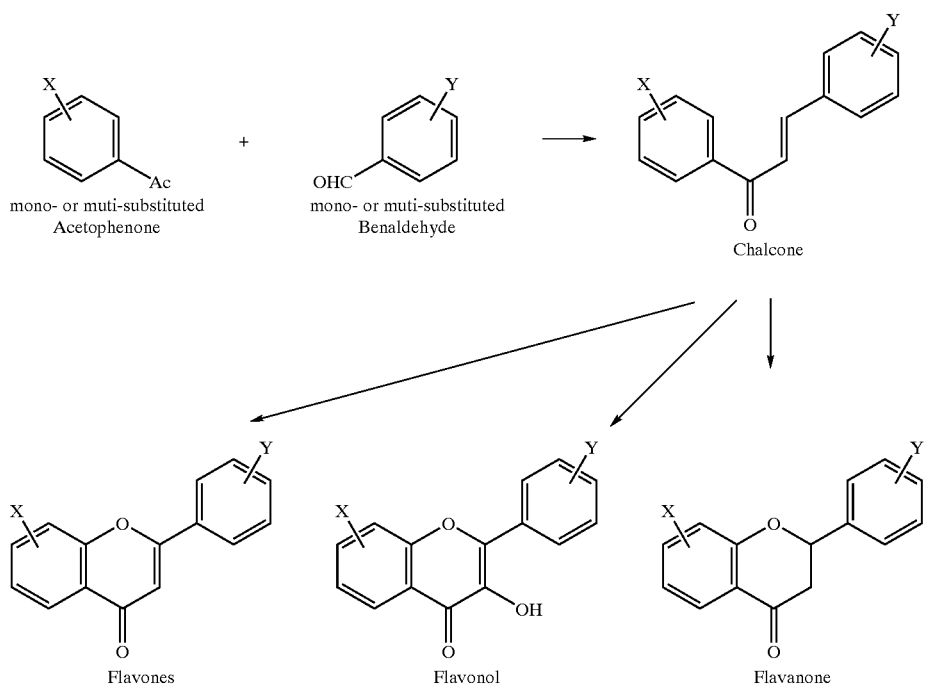

Scheme 1.
Preparation of Chalcones, Chalcone-like compounds, Flavones and Flavanones 3-Chloro-2'-hydroxychalcone (24). M.p. 108–108.5° C., APCIMS m/z 257.3 [M-H]$^+$ (relative intensity 100%), 259.2 [M-H+2]$^+$(isotope) (58%); IR (KBr) cm$^{-1}$: 3091, 3060, 3017 (aromatic CH, =C—H), 3010–2800 (br, —O—H), 1647 (chalcone C=O), 1582, 1492 (arom.); $^1$H-NMR δ (CDCl$_3$)(Ppm): 12.710 (1H, s, OH-2'), 7.923 (1H, dd, J=8.1 Hz, 1.5 Hz, H-6'), 7.846 (1H, d, J=15.6 Hz, H-β), 7.657 (1H, d, J=1.5 Hz, H-2), 7.651 (1H, d, J=15.6 Hz, H-α), 7.552–7.749 (2H, m, H-5',6), 7.45–7.35 (2H, m, H-4,5), 7.043 (1H, dd, J=8.1 Hz, 1.2 Hz, H-3'), and 6.967 (1H, ddd, J=8.1 Hz, 6.9 Hz, 1.2 Hz, H-4'); $^{13}$C-NMR δ (CDCl$_3$)(ppm): 193.598 (>C=O), 163,792 (=C<), 143.783 (=CH—), 136.756 (=CH—), 136.521 (=C<), 135.165 (=C<), 130.784 (=CH—), 130.382 (=CH—), 129.760 (=CH—), 128.106 (=CH—), 127.119 (=CH—), 121.521 (=CH—), 119.956 (=CH—), 119.03 (=C<), and 118.78 (=CH—).

3-Iodo-2'-hydroxychalcone (MCR242, 40). APCIMS m/z 349.1 [M-H]$^+$; IR (KBr) cm$^{-1}$: 3010–2800 (br, —O—H), 1638 (chalcone C=O), 1564, 1485 (arom.); $^1$H-NMR δ (CDCl$_3$)(Ppm): 12.712 (1H, s, OH-2'), 8.019 (1H, d, J=1.5 Hz, H-2), 7.923 (1H, dd, J=8.1 Hz, 1.5 Hz, H-6), 8.798 (1H, d, J=15.6 Hz, H-β), 7.756 (1H, dd, J=7.5 Hz, 1.5 Hz, H-6), 7.625 (1H, d, J=15.6 Hz, H-α), 7.603 (1H, dd, J=7.8 Hz, 1.2 Hz, H-6'), 7.519 (1H, t,d, J=7.8 Hz, 1.2 Hz, H5), 7.179 (1H, t, J=8.4 Hz, H-5'), 7.040 (1H, dd, J=7.2 Hz, 1.2 Hz, H-3'), 6.966 (1H, ddd, J=8.2 Hz, 7.2 Hz, 1.2 Hz, H-4'). $^{13}$C-NMR δ (CDCl$_3$)(ppm): 193.578 (>C=O), 163.818 (>C=), 143.649 (=CH—), 139.665 (=CH—), 137.070 (=CH—), 136.903 (>C=), 136.774 (=CH—), 130.764 (=CH—), 129.816 (=CH—), 128.184 (=CH—), 121.431 (=CH—), 119.982 (>C=), 119.056 (=CH—), 118.805 (=CH—), 94.880 (>C=).

1-(4-Fluorophenyl)-3-(pyridin-3-yl)-2-propen-1-one (53).$^{32}$ M.p. 126–127° C., colorless crystals, APCIMS m/z 228.2 [M+H]$^+$. $^1$H-NMR δ (CDCl$_3$)(ppm): 8.866 (1H, d, J=1.8 Hz, H-2), 8.638 (1H, dd, J=4.8 Hz, 1.5 Hz,H-4), 8.0 (2H, ddd, J=9Hz, Hz, H-2',6'), 7.958 (1H, dt, J=8.1 Hz, 2.1 Hz, H-6), 7.805 (1H, d, J=15.9 Hz, H-P), 7.580 (1H, d, J=15.9 Hz, H-α), 7.380 (1H, dd, J=7.8 Hz, 4.8 Hz, H-5), 7.203 (ddd, H=9.0Hz, 8.1 Hz, 2.1 Hz, H-3',5'). $^{13}$C-NMR δ (CDCl$_3$)(ppm): 188.321 (=C<), 167.628 (=C<), 164.236 (=C<), 151.314 (=CH—), 150.061 (=CH—), 141.252 (=CH—), 134.726 (=CH—), 134.180 (=C<), 131.319 (=CH—), 131.198 (=CH—), 130.638 (=C<), 123.867 (=CH—), 123.435 (=CH—), 116.105 (=CH—), 115.817 (=CH—).

1-(3-Hydroxyphenyl)-3-phenanthren-9-yl-2-propen-1-one (54). M.p. 212–213° C., colorless crystals, APCIMS m/z 325.1 [M+H]$^+$. $^1$H-NMR δ (Acetone-d$_6$)(ppm): 8.926 (1H, m, H-8), 8.86 (1H, d, J=8.1 Hz, H-5), 8.781 (bs, OH), 8.643 (1H, d, J=15.6 Hz, H-β), 8.478 (1H, s, H-10), 8.360 (1H, m, H-4), 8.09 (1H, dd, J=7.8 Hz, 1.8 Hz, H-1), 7.964 (1H, d, J=15.5 Hz, H-α), 7.818–7.643 (6H, m, H-2,3,6,7,2',6'), 7.442 (1H, t, J=7.8 Hz, H-5'), 7.167 (1H, dt, J=7.2 Hz, H-4'). $^{13}$C-NMR δ (Acetone-d$_6$)(ppm): 190.016 (>C=O), 158.956 (=C<), 140.729 ((=C<), 141.905 (=CH—), 132.465 (=C<), 132.276 (=C<), 132.207 (=C<), 131.562 (=C<), 131.373 (=C<), 130.910 (=CH—), 130.432 (=CH—), 128.944 (=CH—), 128.383 (=CH—), 128.163 (=CH—), 128.231 (=CH—), 127.768 (=CH—), 126.425 (=CH—), 125.226 (=CH=), 124.467 (=CH—), 123.799 (=CH—), 121.143 (=CH—), 121.022 (=CH—), and 115.892 (=CH—).

1-(Furan-2-yl)-3-phenyl-2-propen-1-one (MCR211, 56).$^{33}$ M.p. 94–95° C., colorless crystals, APCIMS m/z 199.1 [M+H]$^+$. $^1$H-NMR δ (CDCl$_3$)(Ppm): 7.890 (1H, d, J=15.9 Hz, H—), 7.661 (1H, dd, J=1.5 Hz, 0.9 Hz, H-5'). 7.659 (2H, m, H-2,6), 7.46 (1H, d, J=15.6 Hz, H—), 7.421 (3H, m, H-3,4,5), 7.341 (1H, dd, J=3.3 Hz, 0.9 Hz, H-3'), 6.603 (1H, dd, J=3.6 Hz, 1.5 Hz, H-4'). $^{13}$C-NMR δ (CDCl$_3$) (ppm): 178.195 (>C=O), 153.822 (=C<, C-2'), 146.636 (=CH—, C-5'), 144.101 (C—), 134.814 (=C<, C-1), 130.686 (=CH—, C-4), 129.016 (=CH—, C-3,5), 128.607 (=CH—, C-2,6), 121.216 (=CH—, C-4'), 117.566 (=CH—, C—), 112.596 (=CH—, C-3').

EXAMPLE 2

Flavones

Flavones were synthesized by treating the corresponding chalcones, prepared by the method described above, with selenium dioxide in amyl alcohol. Thus, 2'-, 3'- and 4'-monohalogenoflavones were prepared as usual by condensation of hydroxyacetophenone with o-, m- and p-halogenobenzaldehydes to provide chalcones. This was followed by cyclization of the chalcones with selenium dioxide in amyl alcohol.[17-19] 6-Fluoro-, 6-chloro- and 6-bromoflavones and related compounds were prepared from 2-hydroxy-5-halogenoacetophenones.[19]

EXAMPLE 3

Flavonols

Flavonols were prepared by treating the corresponding chalcones with a 16% solution of aqueous sodium hydroxide and a 15% solution of hydrogen peroxide (v/v 1:1). The 6-halogenoflavonols were prepared in good yield by cyclization of the corresponding chalcones in cold alkaline hydrogen peroxide.[20,21]

EXAMPLE 4

Flavanones

Flavanones were prepared by refluxing the corresponding chalcones with phosphoric acid in alcohol for 2–3 days. Generally, 2-hydroxy-5-halogenoacetophenones condensed smoothly with benzaldehyde or p-anisaldehyde in the presence of alcoholic alkali, giving chalcones, which were cyclized in phosphoric acid to obtain 6-halogenoflavanones.[22]

5-Methoxy-8-bromo-flavanone (MCR264, 133). M.p. 134–165° C., colorless crystals, APCIMS m/z 333.1 [M]$^+$ (relative intensity 100%), 335.0 [M+2]$^+$ (94%); $^1$H-NMR δ (CDCl$_3$)(ppm): 7.656 (1H, d, J=8.7 Hz, H-6), 7.511 (2H, dt, J=7.5 Hz, 1.8 Hz, H-2',6'), 7.526–7.360 (5H, m, B-ring protons), 6.495 (1H, d, J=9.0 Hz, H-7), 5.572 (1H, H-2), 3.030 (2H, m, H-3α and H-3β). $^{13}$C-NMR δ (CDCl$_3$)(ppm): 190.132 (>C=O), 160.211 (=C<), 158.959 (=C<), 138.964 (=CH—), 138.296 (=C<), 128.887 (=CH—), 128.652 (=CH—), 125.844 (=CH—), 112.474 (=C<), 105.326 (=CH—), 102.534 (=C<), 78.034 (=CH—, C-2), 58.353 (—CH$_3$, 5-OCH$_3$), and 45.297 (>CH$_2$, 3-C).

EXAMPLE 5

Biflavonoids

Naturally occurring biflavanoids amentoflavone, agathisflavone, robustaflavone, hinokflavone, rhusflavanone, succedaneaflavanone, volkensiflavone, morelloflavone and GB-1a were isolated from *Rhus succedanea* and *Garcinia multiflora*.[23-28] Synthetic C-C linkage biflavonoids were synthesized by Ulman condensation of monohalogenoflavones.[17c,29,30] Hexa-O-methyl-8,8"-binaringenin was obtained from acidic cyclization of the corresponding bichalcone, which was prepared by Friedel-Crafts reaction of 2,2',4,4',6,6'-hexamethoxybiphenyl with acetic anhydride and anhydrous aluminum chloride in nitrobenzene by refluxing with alcoholic H$_3$PO$_4$ for two weeks.[31]

6,6"-Biapigenin hexamethylether (MCR 408, 151). 6,6"-Biapigenin hexamethylether (151) was synthesized by a three-step synthesis from 4,4'-dibenzyloxy-2,2',6,6'-tetramethoxybiphenyl, which was prepared from the Ullmann reaction of benzyl 4-iodo-3,5-dimethoxyphenylether.[34] Hoesch reaction on 4,4'-dibenzyloxy-2,2',6'6'-tetramethoxybiphenyl with $CH_3CN$, $ZnCl_2$ and HCl in dry $CHCl_3$-$Et_2O$ (1:1) yielded the key product, 4,4'-dihydroxy3,3'-diacetyl-2,2',6'6'-tetramethoxybiphenyl, followed by treatment with two moles of p-anisaldehyde in the presence of alkali to afford the bichalcone. Oxidative cyclization of the bichalcone with $SeO_2$ in dioxane followed by preparative TLC afforded 6,6"-biapigenin hexamethylether, m.p. 303–304° C., colorless crystals, APCIMS m/z 623.3 $[M+H]^+$;

$^1$H-NMR δ ($CDCl_3$)(ppm): 7.862 (4H, d, J=9.3 Hz, H-2', 6',2''',6'''), 7.454 (2H, s, H-8, 8"), 7.026 (4H, J=8.4 Hz, H-3',5',3''',5'''), 6.781 (2H, s, H-3,3"), 4.344 (6H, s, 5,5"-$OCH_3$) and 3.899 (12H, s, 7,7",4',4'''-$OCH_3$).

*Volkensiflavone hexamethylether* (MCR360, 152). Volkensiflavone hexamethyl-ether was prepared from volkensiflavone, which was isolated from the methanol extract of *Garcinia multiflora*.[28]

Isolation of volkensiflavone: The dried heartwood of *Garcinia multiflora* (shavings, 3 kg) was extracted with boiling methanol (4 times). The extract was evaporated to yield a brown oily material, which was extracted with toluene to remove oily substances. The insoluble part was extracted with ethyl acetate. The ethyl acetate extract yielded a light brown solid (25 g) which was chromatographed on 500 g of silica gel, eluting with toluene-ethyl acetate (1:2) to provide fractions I (4 g), II (0.3 g) and III (1.7 g). Fraction I was further chromatographed on a column of polyamide (nylon 66, 200 g), eluting with 70% aqueous methanol to provide fractions Ia (0.1 g), Ib (0.6 g), Ic (0.35 g) and Id (0.5 g). Recrystallization of fraction Id with ethyl acetate/methanol yielded 0.3 g of volkensiflavone as a yellow powder.

Methylation of volkensiflavone: 200 mg of volkensiflavone was dissolved in 20 mL of dry acetone and 2.5 mL of dimethylsulfate and 2 g of potassium carbonate were added. The solution was refluxed for 4 hr, and then filtered. The filtrate was concentrated and purified by silica gel column chromatography using a mixture of toluene and ethyl acetate in a ratio of 1:2 as the eluting solvent. Fractions containing volkensiflavone hexamethylether were combined and concentrated to leave an ivory solid which was recrystallized from a solvent mixture of chloroform and methanol to obtain volkensiflavone hexamethylether as colorless crystals, 138 mg, m.p. 258–260° C., EIMS m/z 624 $[M]^+$, IR (KBr) $cm^{-1}$: 2900, 2950,2850 (OMe), 1680 (flavanone >CO), 1645 (flavone >CO), 1600, 1580, 1510, 1490 (arom.); $^1$H-NMR δ ($CDCl_3$)(ppm): 7.70 (2H, d, J=9 Hz, H-2''',6'''), 7.13 (2H, J=9 Hz, H-2',6'), 6.87 (2H, d, J=9 Hz, H-3''',5'''), 6.63 (2H, d, J=9 Hz, H-3',5'), 6.50 (1H, s, H-3"), 6.30 (1H, d, J=2Hz, H-8), 6.23 (1H, s, H-6"), 6.20 (1H, d, J=2 Hz, H-6), 5.80 (1H, d, J=12 Hz, H-2-H), 4.90 (1H, d, J=12 Hz, H-3), six methoxyl groups at 3.93 (3H, s), 3.87 (3H, s), 3.83 (6H, s), 3.77 (3H, s), 3.67 (3H, s).

EXAMPLE 6

In Vitro Evaluation of Anti-tuberculosis Activity[35-38]

The screening was conducted at a drug concentration of 12.5 μg/mL against Mtb H38Rv in BACTEC 12B medium using a BACTEC 460 radiometric system. The assay procedure was carried out according to the method described previously.[39] Compounds were solubilized in dimethylsulfoxide at 1 mg/mL and sterilized by passage through 0.22 μm PFTE filters. A volume of 50 μL was added to 4 mL BACTEC 12B medium (Becton Dickinson) to achieve a final concentration of 12.5 μg/mL. Approximately 4×105 colony forming units of *M. tuberculosis* H37Rv (ATCC 27294) were added and the cultures were incubated at 37° C. Starting on the second day of incubation, the Growth Index (GI, 1 GI unit=0.0025 dpm $^{14}CO_2$) was determined daily until the controls (drug-free) achieved a GI of 999. The percent inhibition was calculated as 1−(test sample GI÷control GI)×100. The test compounds and results are summarized in Tables 1–5.

Among 179 compounds screened, eight compounds, including biflavonoids, chalcones and chalcone-like compounds, demonstrated >90% inhibition against Mtb H37Rv at a drug concentration of 12.5 μg/mL. Forty-one compounds exhibited activity between 50–89% (80–89%: eight compounds; 70–79%: seven compounds; 60–69%: fourteen compounds; 50–59%: twelve compounds). And seventy-three compounds displayed activity less than 50% (40–49%: fifteen compounds; 30–39%: six compounds; 20–29%: eighteen compounds; 10–19%: sixteen compounds; 1–9%: eighteen compounds). The remaining forty-eight compounds were inactive against Mtb H37RV under the test conditions described above.

Chalcones (1,3-Diaryl-2-propen-1-ones)

The results of anti-TB screening of chalcones are displayed in Table 1. Chalcones with a 2-hydroxyl group in the A ring and a 3-iodo or 3-chloro group in the B ring (40 and 24, respectively) demonstrated the strongest activity among this series of compounds (92% and 90% inhibition against Mtb at a drug concentration of 12.5 μg/mL, respectively). Chalcones without halogen substitution in the molecule exhibited less activity compared to those with a halogen substitution. Introducing a methoxyl group at the 4'-position of compound 40 to derive compound 43 resulted in a dramatic decrease in activity [43 (47%) compared to 40 (92%)].

The activity of 2'-hydroxychalcone (61% inhibition) was enhanced by introducing a chloro or a methoxyl group at the 4'-position of the A-ring, e.g. compound 25 (89%), and 1 (78%), while a bromo, or a iodo substituent at the 4'-position of the B-ring led to a decrease in activity, e.g. 35 (57%) and 21 (45%). The effect of a substituent at the 4'-position of the A-ring of 2'-hydroxy chalcone for anti-TB activity was Cl [25 (89%)]>$OCH_3$ [1 (78%)]>no substituent [5 (61%)]>Br [35 (57%)]>I [21 (45%)]. The bromo substitution at the 3'-position of the A-ring of 2'-hydroxychalcone slightly increased the activity [32 (79%) vs. 5 (61%)]. The effect of substituent at the 5'-position of the A-ring of 2'-hydroxychalcone was Br [34 (68%)]≅phenyl [3 (68%)] ≅Cl [26 (67%)]>H [5 (61%)]>I [42 (51%)]>$NH_2$ [12 (6%)]. The effect of a substitution of a halogen group at a different position of the A-ring of 2'-hydroxychalcone was 4'-[25 (89%)]>5'-[26 (67%)] for chloro substituents, 3'-[32 (79%)] >5'-[34 (68%)]>4'-[35 (57%)] for bromo substituents and 5'-[42 (52%)]>4'-[45 (21%)]>3'-[47 (0%)] for iodo substituents. Introducing an additional substituent on either the A- or B-ring of the above 2'-hydroxychalcones resulted in decreasing or abolishing the activity, e.g. 25 (89%) vs. 28 (57%), 1 (78%) vs. 7 (40%), 34 (68%) vs. 37 (23%) and 38 (8%), 26 (67%), vs. 29 (20%), 35 (57%) vs. 36 (25%) and 38 (12%), 42 (51%) vs. 48 (0%) and 47 (0%) vs. 49 (0%).

The substitution of a halogen group on the B-ring of 2'-hydroxychalcone led to an increase in the anti-TB activity. Compounds with a halogen substituent at the 3-position demonstrated stronger activity than those with a substituent of a halogen at the 2-position or 4-position, such as 40 (92%), 44 (41%) and 46 (21%) for 3-, 2- and 4-iodo substitution, respectively; 31 (83%) and 33 (70%) for 2- and 4-bromo substitution, respectively; 24 (90%) and 27 (67%) for 3- and 4-chloro substitution, respectively. Introducing an additional substituent, such as a methoxyl, bromo or carboxyl group on the A-ring of 2'-hydroxy-3-iodochalcone (40) led to a dramatic decrease or complete loss of activity, e.g. 43 (47%), 50 (0%) and 51 (0%) for 4'-methoxy-, 5'-carboxyl- and 3'-bromo-2'-hydroxy-3-iodochalcone, respectively.

Substitution of a 2'-hydroxyl group in 2'-hydroxy-2-iodochalcone [44 (41%)] with an amino group at the 3'-position dramatically increased the activity [41 (88%)].

Chalcone-Like Compounds (1,3-Disubstituted 2-propen-1-ones)

Chalcone-like compounds demonstrated the most significant anti-TB activity among all the compounds evaluated, including chalcones, flavonoids and biflavonoids. As presented in Table 2, compounds 53, 54, 55, and 56 inhibited 98%, 97%, 96% and 96% growth of Mtb H37Rv at a drug concentration of 12.5 µg/mL, respectively. The common structural feature of these four compounds is that they all have a heterocyclic ring or a phenyl ring with a hydrophilic group substituent on one side of the molecule, and an aromatic ring, such as phenyl or phenanthrenyl, with or without a hydrophobic substituent on the other side. Additional hydrophylic substituents, such as methoxyl, hydroxyl and amino groups resulted in dramatic decrease or complete loss of activity. From the above results, active compounds resulted from structures having a lipophilic group on one side and a hydrophilic group on the other side of the 2-propen-1-one core template.

Flavones

The anti-TB activities of flavones are presented in Table 3. All flavones tested, including carboxylated, halogenated, hydroxylated and methoxylated flavones were only moderately to weakly active or inactive, while halogenated flavones or halogenated flavonols (3-hydroxyflavones) demonstrated moderate activity. Flavones with bromine or chlorine substitution at the 8-position displayed inhibitory activity against Mtb with 66% and 62% growth inhibition at a dose of 12.5 µg/mL, respectively, while the flavones with a halogen substitution at the 3-position (compound 127), 6-, 7-, or 8-position of ring A (compounds 102, 105, 106, 112, 114, 122, 123 and 124) and 2', 3', or 4'-position of ring B (compounds 84, 97, 99, 100, 101, 111 and 121) were weakly active or inactive. Flavonol (3-hydroxyflavone) (92) exhibited weak activity of 38% inhibition. The substitution of a methoxyl group at the 4'-position of flavonol (88) led to a small increase in activity (10% increase compared to 92). Further substitution of a 6-Cl or a 7-F- group on 4'-methoxyflavonol (87 and 85) did not change the activity. However, a substitution of an iodo group at the 7 or 8-position, or a fluoro or a bromo group at the 6-position or a carboxyl group at the 6-position of 4'-methoxyflavonol resulted in significant decreases in, or complete loss of, activity.

Flavanones

Eighteen flavanones were evaluated for anti-TB activity. The results are listed in Table 4. 5-Methoxy-8-bromoflavanone (133) demonstrated the most significant activity among these flavanones, with 87% inhibition against Mtb. The substitution of a bromo group on the B-ring demonstrated higher activity than that on the A-ring [3'-bromo-(134), 73%, versus 7-bromo-flavanone (136), 53%].

Biflavonoids

The results of anti-TB activity of biflavonoids are presented in Table 5. Methoxylated biflavonoids 6,6"-biapigenin hexamethylether (151), volkensiflavone hexamethylether (152) and GB-la hexamethylether (153) demonstrated strong inhibitory activity against Mtb with 96%, 95% and 87% growth inhibition at a concentration of 12.5 µg/mL, respectively. These biflavonoids were composed of two apigenin units through a I6–II6 linkage, one naringenin and one apigenin unit or two narigenin units with thea linkage at the I3–II8 position (3-position of unit I linked to 8-position of unit II) (152 and 153).

Biflavonoid methylethers constructed with two flavone units or with a flavone and a flavanone unit displayed equal strength of activity (151 and 152). A biflavonoid methylether (153) constructed with two flavanone units demonstrated less activity than that constructed with a flavone and a flavanone (152) (87% versus 95% inhibition), although both compounds have the same linkage structure (I3–II8). Biapigenin hexamethylether with a linkage of I3–II3 (159) was completely devoid of activity. This result indicated that the I6–II6 linkage might be important for the activity. Comparison of the inactive binaringenin hexamethylether constructed by two units of naringenin trimethylether through a I6–II6 linkage (157) to the active compounds 151 and 153, it was

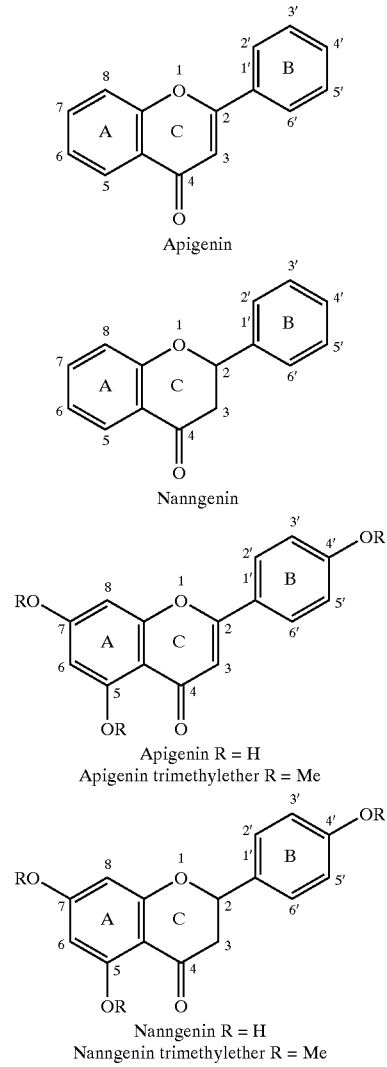

Scheme 2.
Structures of Flavonoids and Biflavonoids

Apigenin

Nanngenin

Apigenin R = H
Apigenin trimethylether R = Me

Nanngenin R = H
Nanngenin trimethylether R = Me

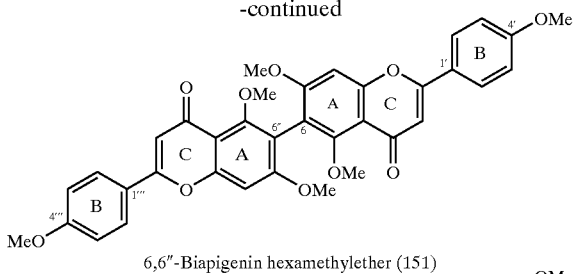

6,6"-Biapigenin hexamethylether (151)

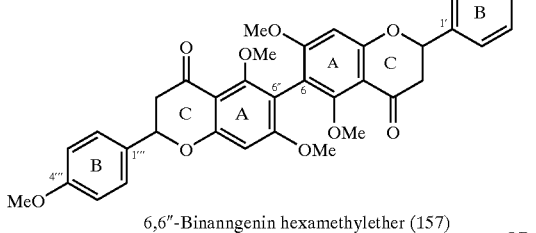

6,6"-Binanngenin hexamethylether (157)

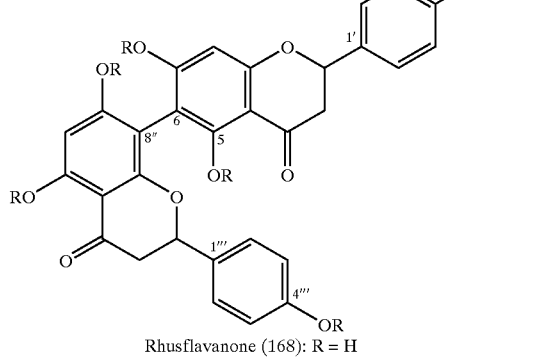

Rhusflavanone (168): R = H
Rhusflavanone hexaacetate (173): R = COMe

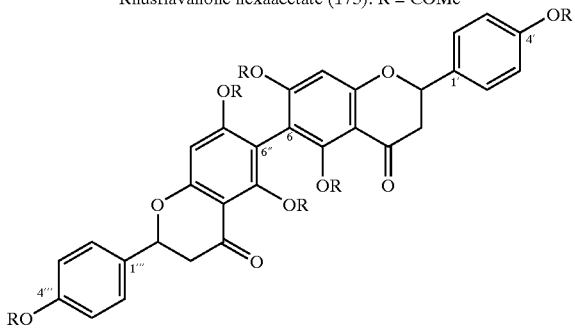

Succedaneaflavanone (169): R = H
Succedaneaflavanone hexaacetate (174): R = COMe

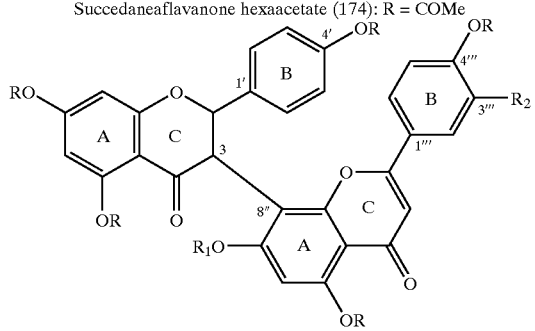

Volkensiflavone (170): R = R₁ = R₂
Morelloflavone (171): R = R₁ = H, R₂ = OH
Spicataside (176): R = R₂ = H, R₁ = Glucosyl
Volkensiflavone hexamethylether (152): R = R₁ = Me, R₂ = H
Morelloflavone heptaacetate (175): R = R₁ = COMe, R₂ = OCOMe
Spicataside acetate (177): R = COMe, R₁ = acetyl glucosyl

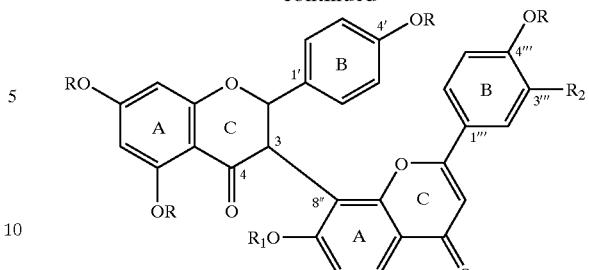

GB-2a (172): R = $R_1$ = H, $R_2$ = OH
GB-1a- glucoside (178): R = $R_2$ = H, $R_1$ = glucosyl
Xanthochymuside (179): R = H, $R_1$ = glucosyl, $R_2$ = OH
GB-1a hexamethylether (153): R = $R_1$ = Me, $R_2$ = H observed that two units of the flavone structure were necessary for the activity of biflavonoids with a I6–II16 linkage and I3–II8 linkage was important for the activity of biflavonoids composed of a flavanone and a flavone unit. Hydroxylated biflavonoids, biflavonoid glucosides or unsubstituted biflavonoids were inactive with the exception that I3'–II8"-biflavone (155) exhibited moderate activity. This result indicated that the lipophilic property of a compound might be important for the activity.

In conclusion, two chalcone compounds (24 and 40) and four chalone like compounds (heterocyclic ring substituted 2-propen-1-ones) (53, 54, 55 and 56) exhibited greater than 90 percent inhibition against Mtb. The common structural features of these six compounds are that all the compounds have two aromatic rings, one ring substituted with a heteroatom and the other with or without hydrophobic substitutions. Introduction of extra hydrophilic substituents such as methoxyl, hydroxyl and amino groups would render the compounds less active. With the exception of compound 53, the other five compounds all have a hydrogen-bonding group substituted on the A-ring, while the B-ring remained hydrophobic. Structural superposition analysis indicateed that compound 53 can actually be superimposed on the other five compounds the other way. For example, compound 53 can superimpose its A-ring with the B-ring of compound 56, while keeping its B ring superimposed with the A ring of compound 56 (Scheme 2).

Flavones and flavanones can be viewed as geometrically constrained chalcone analogues. It may indeed be due to these structural constraints that they are less active compared to chalcones. Some examples illustrate the relationship of activity between a chalcone and its corresponding flavone, i.e., when a chalcone was converted to its corresponding flavone, the anti-TB activity decreased. Examples of this include compound 44 being converted to compound 100 in which activity decreased from 41% to 22%; 44 to 100, 41% to 22%; 31 to 99, 83% to 23%; 33 to 97, 70% to 26%, 24 to 121, 90% to 0%; and 27 to 111, 67% to 7%. The only exception to this pattern was compound 46 being converted to compound 84 (21% to 51%).

Compared to flavanones, flavones are less active, and are structurally more restricted, with the two terminal aromatic rings in the same plane. The structures of the biflavonoids are apparently different from that of chalcone and flavanoid monomers. The two active biflavonoids have only methoxyl substitutions (a methoxyl group is not a good hydrogen bonding group), while the chalcone and chalcone-like compounds prefer a hydroxyl or other hydrogen bonding group. Without being bound by any theory of operation for this invention, most probably, the biflavonoids kill Mtb by a different mechanism.

TABLE 1

Anti-tuberculosis Activity of Chalcones

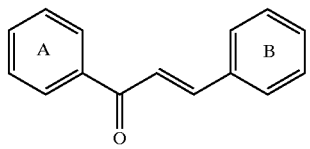

| Compds | A-ring 2'- | 3'- | 4'- | 5'- | 6'- | B-ring 2- | 3- | 4- | 5- | Activity % inhibition at 12.5 μg/mL |
|---|---|---|---|---|---|---|---|---|---|---|
| 1 MCR206 | OH | | OCH₃ | | | | | | | 78 |
| 2 MCR202 | OH | | | OCH₃ | | | | OCH₃ | | 75 |
| 3 MCR251 | OH | | | phenyl | | | | | | 68 |
| 4 MCR388 | | | NO₂ | | | | | OCH₃ | | 62 |
| 5 MCR201 | OH | | | | | | | | | 61 |
| 6 MCR222 | | OH | | | | | OCH₂– | O– | | 53 |
| 7 MCR205 | OH | | OCH₃ | | OCH₃ | | | OCH₃ | | 40 |
| 8 MCR208 | OH | | | | | OCH₃ | | | | 39 |
| 9 MCR209 | OH | | OCH₃ | | | | | OCH₃ | | 32 |
| 10 MCR210 | OH | | | | | | | OH | | 18 |
| 11 MCR255 | OH | | | | | | | NH₂ | | 11 |
| 12 MCR256 | OH | | | NH₂ | | | | | | 6 |
| 13 MCR385 | | | NH₂ | | | | | | | 5 |
| 14 MCR203 | OH | | EtO | | EtO | | | | | 0 |
| 15 MCR207 | OH | | OCH₃ | | OH | | OCH₃ | OCH₃ | OCH₃ | 0 |
| 16 MCR250 | OH | | COOH | | | | | OCH₃ | | 0 |
| 17 MCR253 | OH | | | | | | | NHCOCH₃ | | 0 |
| 20 MCR216 | F | | | | | | | OCH₃ | | 82 |
| 21 MCR214 | OH | | | | F | | | OCH₃ | | 66 |
| 22 MCR217 | OH | | F | | | | | OCH₃ | | 63 |
| 23 MCR215 | OH | F | | | | | | OCH₃ | | 45 |
| 24 MCR224 | OH | | | | | | | Cl | | 90 |
| 25 MCR226 | OH | | Cl | | | | | | | 89 |
| 26 MCR228 | OH | | | Cl | | | | | | 67 |
| 27 MCR223 | OH | | | | | | | Cl | | 67 |
| 28 MCR225 | OH | | Cl | | | | | OCH₃ | | 57 |
| 29 MCR227 | OH | | | Cl | | | | OCH₃ | | 20 |
| 30 MCR343 | | OH | | | | | | Cl | | NA |
| 31 MCR234 | OH | | | | | Br | | | | 83 |
| 32 MCR235 | OH | Br | | | | | | | | 79 |
| 33 MCR230 | OH | | | | | | | Br | | 70 |
| 34 MCR233 | OH | | | Br | | | | | | 68 |
| 35 MCR232 | OH | | Br | | | | | | | 57 |
| 36 MCR236 | OH | | Br | | | | | OCH₃ | | 25 |
| 37 MCR237 | OH | | | Br | | | | OCH₃ | | 23 |
| 38 MCR345 | OH | | Br | | | NH₂ | | | | 12 |
| 39 MCR346 | OH | | | Br | | NH₂ | | | | 8 |
| 40 MCR242 | OH | | | | | | | I | | 92 |
| 41 MCR347 | | NH₂ | | | | | | I | | 88 |
| 42 MCR218 | OH | | | I | | | | | | 51 |
| 43 MCR246 | OH | | OCH₃ | | | | | I | | 47 |
| 44 MCR244 | OH | | | | | I | | | | 41 |
| 45 MCR240 | OH | | I | | | | | | | 21 |
| 46 MCR245 | OH | | | | | | | I | | 21 |
| 47 MCR239 | OH | I | | | | | | | | 0 |
| 48 MCR243 | OH | | | I | | | | OCH₃ | | 0 |
| 49 MCR248 | OH | I | | | | | | OCH₃ | | 0 |
| 50 MCR238 | OH | | | COOH | | | | I | | 0 |

*-: not tested

TABLE 2

Anti-Tuberculosis Activity of Chalcone-like Compounds

| Compounds | R | R' | Activity % inhibition at 12.5 μg/mL |
|---|---|---|---|
| 53 MCR340 | 4-fluorophenyl- | pyridin-3-yl- | 98 |
| 54 MCR349 | 3-hydroxyphenyl- | phenanthren-9-yl- | 97 |
| 55 MCR350 | pyridin-3-yl- | phenanthren-9-yl- | 96 |
| 56 MCR211 | furan-2-yl- | phenyl- | 96 |
| 57 MCR383 | phenanthren-2-yl- | 2-aminopyridino-3-yl- | 74 |
| 59 MCR382 | 3-fluorenyl- | 2-aminopyridino-3-yl- | 53 |
| 60 MCR390 | pyridin-2-yl- | pyridin-2-yl- | 42 |
| 61 MCR252 | naphthalen-1-yl- | phenyl- | 37 |
| 62 MCR391 | pyridin-2-yl- | 4-dimethylaminophenyl- | 16 |
| 63 MCR221 | 4-bromo-2-hydroxyphenyl- | furan-2-yl- | 17 |
| 64 MCR348 | pyridin-4-yl- | indol-2-yl- | 12 |
| 65 MCR212 | 2-hydroxy-4-methoxyphenyl- | furan-2-yl- | 3 |
| 66 MCR379 | 4-aminophenyl- | 2-aminopyridin-3-yl- | 7 |
| 68 MCR392 | pyridin-4-yl- | 4-dimethylaminophenyl- | 1 |
| 69 MCR213 | 2-hydroxy-5-methoxyphenyl- | furan-2-yl- | 0 |
| 70 MCR338 | 4-methoxyphenyl- | pyridin-4-yl- | 0 |
| 71 MCR339 | 4-methoxyphenyl- | pyridin-3-yl- | 0 |
| 72 MCR341 | 2-hydroxy-5-chlorophenyl- | 2-amino-pyridin-3-yl- | 0 |
| 73 MCR380 | 4-aminophenyl- | 2-aminopyridin-3-yl- | 0 |
| 74 MCR381 | 3-hydroxynaphthalen-2-yl- | 2-aminopyridin-3-yl- | 0 |
| 75 MCR386 | furan-2-yl- | pyridin-4-yl- | 0 |
| 76 MCR389 | pyridin-2-yl | 4-methoxyphenyl- | 0 |

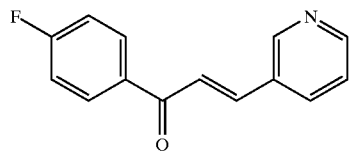

53

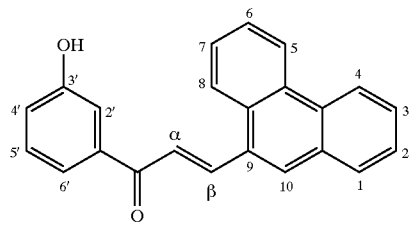

54

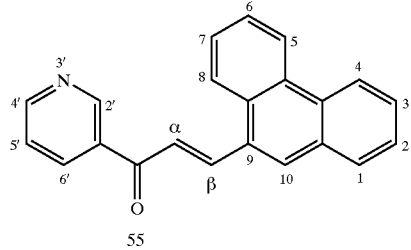

55

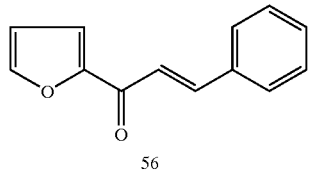

56

TABLE 3

Anti-tuberculosis Activity of Flavones

| Compds | 3 | 5 | 6 | 7 | 8 | 2' | 3' | 4' | 5' | Activity % Inhibition at 12.5 μg/mL |
|---|---|---|---|---|---|---|---|---|---|---|
| 77 MCR293 | | | | | Br | | | | | 66 |
| 78 MCR288 | | | | | Cl | | | | | 62 |
| 79 MCR329 | OH | | I | | | | | | | 64 |
| 80 MCR322 | OH | | | | | | Br | | | 60 |
| 81 MCR317 | OH | | | Cl | | | | | | 58 |
| 82 MCR319 | OH | | Br | | | | | | | 58 |
| 84 MCR303 | | | | | | | | I | | 51 |
| 85 MCR312 | OH | | | F | | | | OCH₃ | | 50 |
| 86 MCR314 | OAc | | | F | | | | OCH₃ | | 50 |
| 87 MCR316 | OH | | Cl | | | | | OCH₃ | | 48 |
| 88 MCR332 | OH | | | | | | | OCH₃ | | 48 |
| 89 MCR323 | OCH₃ | | Br | | | | | | | 44 |
| 90 MCR315 | OH | | | F | | | | | | 43 |
| 91 MCR328 | OH | | | I | | | | OCH₃ | | 43 |
| 92 MCR309 | OH | | | | | | | | | 38 |
| 93 MCR275 | | | | | | | | OCH₃ | | 29 |
| 94 MCR311 | OH | | F | | | | | OCH₃ | | 29 |
| 95 MCR306 | | | | | | | NO₂ | Cl | | 28 |
| 96 MCR324 | Br | | | | | | | OCH₃ | | 28 |
| 97 MCR290 | | | | | | | | Br | | 26 |
| 98 MCR320 | OH | | Br | | | | | OCH₃ | | 24 |
| 99 MCR289 | | | | | | | Br | | | 23 |
| 100 MCR295 | | | | | | | I | | | 22 |
| 101 MCR304 | | | | | | | | I | | 22 |
| 102 MCR297 | | | | I | | | | | | 20 |
| 103 MCR298 | Br | | | OCH₃ | | | | Cl | | 19 |
| 104 MCR276 | | | | | | | | OH | | 18 |
| 105 MCR283 | | | | F | | | | | | 15 |
| 106 MCR292 | | | | Br | | | | | | 15 |
| 107 MCR305 | | | I | | | | | OCH₃ | | 15 |
| 108 MCR294 | Br | | | | | | | | | 13 |
| 109 MCR277 | | OCH₃ | | OCH₃ | | | | OCH₃ | | 12 |
| 110 MCR308 | benzoyl | | | benzoyl | | | | | | 12 |
| 111 MCR284 | | | | | | | | Cl | | 7 |
| 112 MCR282 | | | F | | | | | | | 7 |
| 113 MCR330 | OH | | | | I | | | OCH₃ | | 6 |
| 114 MCR296 | | | | | I | | | | | 5 |
| 115 MCR307 | | | COOH | | | | | OCH₃ | | 2 |
| 116 MCR278 | | | | | OH | | | | | 1 |
| 117 MCR274 | | | | OCH₃ | | | | | | 0 |
| 118 MCR280 | | | | F | | | | OCH₃ | | 0 |
| 119 MCR279 | | | | OCH₃ | | | | OCH₃ | | 0 |
| 120 MCR281 | | | F | | | | | OCH₃ | | 0 |
| 121 MCR285 | | | | | | | Cl | | | 0 |
| 122 MCR287 | | | | Cl | | | | | | 0 |
| 123 MCR291 | | | Br | | | | | | | 0 |
| 124 MCR298 | | | I | | | | | | | 0 |
| 125 MCR299 | | OCH₃ | | OCH₃ | I | | | OCH₃ | | 0 |
| 126 MCR299 | | OCH₃ | | OCH₃ | | | I | OCH₃ | | 0 |
| 127 MCR301 | I | | | | | | | | | 0 |
| 128 MCR302 | | | | I | | | | OCH₃ | | 0 |
| 130 MCR331 | OH | | COOH | | | | | OCH₃ | | 0 |
| 131 MCR394 | Br | OCH₃ | | OCH₃ | | | | OCH₃ | | 0 |
| 132 MCR273 | | OCH₃ | | OCH₃ | | | | OH | | 0 |

TABLE 4

Anti-tuberculosis Activity of Flavanones

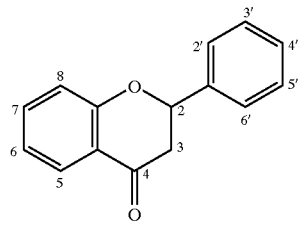

| Compounds | 3 | 5 | 6 | 7 | 8 | 3' | 4' | 5' | Activity % Inhibition at 12.5 μg/mL |
|---|---|---|---|---|---|---|---|---|---|
| 133 MCR264 |  | OCH₃ |  |  | Br |  |  |  | 87 |
| 134 MCR266 |  |  |  |  |  |  | Br |  | 73 |
| 135 MCR333 | OH |  |  |  |  |  | Cl |  | 63 |
| 136 MCR263 |  |  |  | Br |  |  |  |  | 53 |
| 137 MCR261 |  |  |  | OCH₃ |  |  | Cl |  | 48 |
| 138 MCR260 |  |  | Cl |  |  |  |  |  | 30 |
| 139 MCR267 |  |  |  | I |  |  |  |  | 27 |
| 140 MCR265 | Br₂ | OCH₃ |  | OCH₃ | OCH₃ | OCH₃ | OCH₃ |  | 16 |
| 141 MCR268 |  |  |  | I |  |  |  |  | 9 |
| 142 MCR262 |  |  | Br |  |  |  |  |  | 8 |
| 143 MCR259 |  |  |  |  | F |  |  |  | 7 |
| 144 MCR258 |  | OCH₃ |  | OCH₃ | OCH₃ | OCH₃ | OCH₃ |  | 0 |
| 145 MCR271 |  |  | COOH |  |  |  | OCH₃ |  | 0 |
| 146 MCR270 |  |  | COOH |  |  |  |  |  | 0 |
| 147 MCR272 |  |  |  | OCH₃ |  | NO₂ |  |  | 0 |
| 148 MCR335 | Br₂ |  |  |  |  |  |  |  | 0 |
| 149 MCR269 |  |  |  | I |  |  | OCH₃ |  | 0 |

TABLE 5

Anti-tuberculosis Activity of Biflavonoids

| Compds | Name | units | Linkage | Activity % Inhibition at 12.5 μg/mL |
|---|---|---|---|---|
| 151 MCR 408 | 6-6"-Biagpigenin hexamethyleher | Apigenin trimethylether (5,7,4'-trimethoxy-flavone) (I) Apigenin trimethylether (II) | I-6-II-6 | 96 |
| 152 MCR 360 | Volkensiflavone hexamethylether | Naringenin triamethylether (5,7,4'-trimethoxy-flavanone) (I) Apigenin trimethyl ether (II) | I-3-II-8 | 95 |
| 153 MCR 367 | GB-1a hexamethylether | Naringenin triamethylether (I) Naringenin trimethyl ether (II) | I-3-II-8 | 87 |
| 154 MCR 398 | 3'''-Nitro-C3-O-C4''''--Biflavone | Flavone (I) 3'-Nitroflavone (II) | I3'-O-II4' | 61 |
| 155 MCR 406 | 3'-8"-Biflavone | Flavone (I) Flavone (II) | I-3'-II-8 | 49 |
| 156 MCR 400 | 6-2''''-Biflavone | Flavone (I) Flavone (II) | I-6-II-2' | 9 |
| 157 MCR 407 | 6-6"-Binaringenin hexamethylether | Naringenin trimethylether (I) Naringenin trimethylether (II) | I-6-II-6 | 2 |
| 158 MCR 401 | 6-2'''-Biapigenin | Apigenin (I) Apigenin (II) | I-6-II-2' | 1 |
| 159 MCR 403 | 3-3"-Biapigenin hexamethylether | Apigenin trimethylether (I) Apigenin trimethylether (II) | I-3-II-3 | 0 |
| 160 MCR 402 | 3-3"-Bi-(7-methoxyflavanone) | 7-Methoxyflavanone (I) 7-Methoxyflavanone (II) | I-3-II-3 | 0 |
| 161 MCR 399 | 8-2'''-Biflavone | Flavone (I) Flavone (II) | I-8-II-2' | 0 |
| 162 MCR 404 | 7-3'''-Biflavone | Flavone (I) Flavone (II) | I-7-II-3' | 0 |
| 163 MCR 405 | 4'-4'''-Biflavone | Flavone (I) Flavone (II) | I-4'-II-4' | — |
| 164 MCR 351 | Amentoflavone | Apigenin (I) Apigenin (II) | I-3'-II-8 | 0 |
| 165 MCR 352 | Agathisflavone | Apigenin (I) APigenin (II) | I-6-II-8 | 0 |

TABLE 5-continued

Anti-tuberculosis Activity of Biflavonoids

| Compds | Name | units | Linkage | Activity % Inhibition at 12.5 μg/mL |
|---|---|---|---|---|
| 166 MCR 353 | Robustaflavone | Apigenin (I)<br>APigenin (II) | I-3'-II-6 | 0 |
| 167 MCR 354 | Hinokiflavone | Apigenin (I)<br>Apigenin (II) | I-4'-O-II-6 | 0 |
| 168 MCR 355 | Rhusflavanone | Naringenin (I)<br>Naringenin (II) | I-6-II-8 | 0 |
| 169 MCR 357 | Suceedaneaflavanone | Naringenin (I)<br>Naringenin (II) | I-6-II-8 | 0 |
| 170 MCR 359 | Volkensiflavone | Naringenin (I)<br>Apigenin (II) | I-3-II-8 | 0 |
| 171 MCR 363 | Morelloflavone | Naringenin (I)<br>Luteolin<br>(3',4',5,7,-tetrahydroxyflavone) (II) | I-3-II-8 | 0 |
| 172 MCR 369 | GB-2a | Naringenin (I)<br>Eriodictyol<br>(3',4',5,7-tetrahydroxyflavanone) (II) | I-3-II-8 | 0 |
| 173 MCR 356 | Rhusflavanone hexaacetate | Naringenin triacetate ((I)<br>Naringenin triacetate (II) | I-6-II-8 | 0 |
| 174 MCR 358 | Succedaneaflavanone hexaacetate | Naringenin triacetate ((I)<br>Naringenin triacetate (II) | I-6-II-6 | 0 |
| 175 MCR 364 | Morelloflavone heptaacetate | Naringenin triacetate (I)<br>Luteolin tetraacetate<br>(3',4',5,7-tetraacetoxyflavone) (II) | I-3-II-8 | 0 |
| 176 MCR 361 | Spicataside<br>(Volkensiflavone-7-glucoside) | Naringenin (I)<br>Apigenin-7-glucoside (II) | I-3-II-8 | 0 |
| 177 MCR 362 | Spicataside acetate | Naringenin triacetate (I)<br>Apigenin-7-glucoside acetate (II) | I-3-II-8 | 0 |
| 178 MCR 368 | Multifloraside<br>(GB-1a glucoside) | Naringenin (I)<br>Naringenin-7-glucoside (II) | I-3-II-8 | 0 |
| 179 MCR 370 | Xanthochymuside<br>(GB-2a Glucoside) | Naringenin (I)<br>Eriodictyol-7-glucoside (II) | I-3-II-8 | 0 |

Literature Cited

1. Lopez, A. in Disease Control Priorties in Developing Countries, Jamison, D. T., Mosely, W. H. Eds. (Oxford Univ. Press for the World Bank, New York, 1992), p. 21.
2. Murray, C. J. L., Styblo, K., Rouillon, A. in *Disease Control Priorities in Developing Countries*, Jamison, D. T., Mosely, W. H. Eds. (Oxford Univ. Press for the World Bank, New York, 1992), p. 50; Styblo, K. The global aspects of tuberculosis and HIV, *Bull. Int. Union Tuberc.* 1990, 65, 24.
3. Raviglione, M. C., Snider, D. E., Kochi, A. Global Epidemiology of Tuberculosis, JAMA, 1995, 273, 220–226.
4. Ozdemir, F. N., Guz, G., Kayatas, M., Sezer, S., Arslan, H., Turan, M. Tuberculosis Remains an Important Factor in the Morbidity and Mortality of Hemodialysis Patients, *Transplantation Proceedings*, 1998, 30, 846–847.
5. *Wall Street Journal* (May 29, 1998).
6. Harries, A. D., Mahler, D. TB/HIV A Clinical Manual Published by the World Health Organization 1996, Printer: Stabilimento Tipografico Ferrero s. r. 1. -Romano Canavese [TO], Italy.
7. Nivin, B., Nicholas, P., Gayer, M., Frieden, T. R., Fujiwara, P. I. A Continuing Outbreak of Multidrug-Resistant Tuberculosis, with Transmission in a Hospital Nursery, *Clin. Infect. Dis.* 1998, 26, 303–307.
8. Bernstein, J., Lott, W. A., Steinberg, B. A., Yale, H. L. Chemotherapy of Experimental Tuberculosis V. Isonicotinic Acid hydrazide (Nydrazid) and Related Compounds, *Am. Rev. Tuberc.* 1952, 65, 357.
9. Fix, H. H. *Science*, 1952, 116, 129.
10. Pansy, F., Stander, H., Donovick, R. In Vitro Studies on Isonicotinic Acid Hydrazide *Am. Rev. Tuberc.* 1952, 65, 761.
11. Robitzek, E. H., Selikoff, I. J. Hydrazine Derivatives of Isonicotinic Acid (Rimifon, Marsilid) in the Treatment of Active Progressive Caseous-Pneumonic Tuberculosis, *Am. Rev. Tuberc.* 1952, 65, 402.
12. Petersen, Andrea, *Wall Street Journal* (Jun. 24, 1998), pp. B5.
13. Mitchison, D. A. Understanding the Chemotherapy of Tuberculosis—Current Problems, *J. Antimicrob. Chemother.* 1992, 29, 477–493.
14. Pablos-Mendez, A., Raviglione, M. C., Laszlo, A., Binkin, N., Rieder, H. L., Bustreo, F., Cohn, D. L., Lambregts-van Weezenbeek, C. S. B., Kim, S. J., Chaulet, P., Nunn, P. Global Surveillance for antituberculosis-Drug Resistance, 1994–1997, *New Eng. J Med.* 1998, 338, 1641.
15. Kohler and Chadwell, *Org. Synth.* 1922, 2, 1.
16. Ariyan, Z. S., Suschitzky, H. Heterocyclic Compounds of Chalcone Type, *J. Chem. Soc.* 1961, 2242–2244.
17. a. Chen, F. C., Yang, C. H., Hsu, K. K., Synthesis of Halogenoflavonoids I. Synthesis of 6-Chloro-flavanone and -flavone. *J. Formosan Sci.* 1953, 7, 51–53.
    b. Chen, F. C., Hsu, K. K., Synthesis of Halogenoflavonoids II. Synthesis of 2',3',4'-Chloro-flavanone and -flavone. *J. Formosan Sci.* 1953, 7, 54–56.
    c. Chen, F. C., Lai, P. C., Hsieh, H. C., Synthesis of Halogenoflavonoids III. Synthesis of 2'-, 3'-, 4'-, 6-Bromoflavanones and 6-Bromo-flavones. *J. Formosan Sci.* 1953, 7, 57–62.
    d. Chen, F. C., Lin, C., Lai, S. C., Synthesis of Halogenoflavonoids IV. Synthesis of 2'-,3'-, 4'-Iodoflavanone and Corresponding Chalcones. *J. Formosan Sci.* 1953, 7, 63–65.

18. Chen, F. C., Lin, C., Tu,T. T., Synthesis of Halogenoflavonoids VII. Synthesis of 2-, 3- and 4- Fluoro-2'-Oxychalcone. *J. Formosan Sci.* 1954, 8, 71–73.
19. Chang, C. T., Chen, F. C., Chen, T. S., Hsu, K. K., Ueng, T., Hung, M. Synthesis of 6-Halogenoflavones and Relaated Compounds. *J. Chem. Soc.* 1961, 3414.
20. Chen, F. C., Chang, C. T., Synthesis of Halogenoflavonoids VIII. Synthesis of 6-Iodoflavonol, Its corresponding Chalcone and 2-Oxy-5-Iodoacetophenone. *J. Formosan Sci.* 1954, 8, 74–75.
21. Chen, F. C., Hsu, K. K. *J. Taiwan Pharm. Assoc.*, 1953, 5, 49.
22. Chen, F. C., Chang, C. T. Synthesis of 7-halogenoflavone and related compounds. *J. Chem. Soc.* 1958,146–150.
23. Lin, Y. M., Chen, F. C., Liang, C. M. Biflavonyls from drupes of *Rhus succedanea*. *Phytochemistry* 1974, 12, 276–277.
24. Lin, Y. M., Chen, F. C. Agathisflavone from drupes of *Rhus succedanea*. *Phytochemistry* 1974, 13, 657–658.
25. Lin, Y. M., Chen, F. C. Robustaflavone from the seed of kernels of *Rhus succedanea*. *Phytochemistry* 1974, 13, 1617–1619.
26. Chen, F. C., Lin, Y. M. Rhusflavanone, a new biflavanone from the seeds of wax tree. *J. Chem. Soc.*, Perkin Trans. 1976,I 98–101.
27. Chen, F. C., Lin, Y. M. Succedaneaflavone, A new 6,6'-biflavanone from *Rhus succedanea*. *Phytochemistry* 1975, 14, 1644–1647.
28. Chen, F. C., Lin, Y. M., Hung, J. G. Phenolic compounds from the heartwood of *Garcinia multiflora*. *Phytochemistry* 1975, 14, 300–303.
29. Chen, F. C., Chang, C. T., Hong, M., Lin, Y. C., Choong, S. T. *Proc. Chem. Soc*1959, 232
30. Chen, F. C. Studies in the Synthesis of Biflavonyls. *Symposium on Phytochemistry*, Hong-Kong 1961, pp. 166–168.
31. Chen, F. C., Lin, Y. M., Ho, T. I., Ueng, T. Synthesis of Hexa-O-Methyl-8,8"-Binaringenin. *Heterocycles*, 1975, 3, 833–836.
32. Chen, F. C., Chen, Y. H. Chen, C. Y. Synthesis of Azachalcones and Analogs. *J. Formosan Sci.* 1972, 26, 52.
33. Chen, F. C., Chen, Y. H. Chen, L. S. Synthesis of 2-Furylacrylophenones and Analogs. *J. Formosan Sci.* 1972, 26, 50.
34. Chen, F. C, Lin, Y. M., Shue, Y. K., Ueng, T. Synthesis of Hexa-O-Methyl-6,6"-Binaringenin and -Biapigenin, *Heterocycles*, 1975, 3, 529–532.
35. Inderleid, C. B., Nash, K. A. *Antibiotics in Laboratory Medicine*. 4th ed. (Ed: Lorian, V 1996) Williams and Wilkins, Baltimore, p. 127–175.
36. Inderleid, C. B. and M. Salfinger. *Manual of Clinical Microbiology*, 6th Ed. (Eds: Murray, P. R., Baron, E. J., Pfaller, M. A., Tenover, F. C., Yolken, R. H. 1995) ASM Press, Washington D. C. p. 1385–1404.
37. Siddiqi, S. H. Radiometric (BACTEC) tests for slowly growing mycobacteria In: *Clinical Microbiology Procedures Handbook. Vol.* 1. (Ed: Isenberg, HD 1992) American Society for Microbiology, Washington, D. C. p. 5.14.2 –5.14.25.
38. Heifets, L. B. Drug susceptibility tests in the management of chemotherapy of tuberculosisln: *Drug Susceptibility in the Chemotherapy of Mycobacterial Infections*. (Ed: Heifets,L. B. 1991) CRC Press, Boca Raton, p. 89–122.
39. Collins, L. S., Franzblau, S. G. Microplate Alamar Blue assay versus BACTEC 460 system for high throughput screening of compounds against *Mycobacterium tuberculosis* and *Mycobacterium avium*. *Antimicrob. Agents and Chemother*. 1997, 41:1004–1009.

What I claim:

1. A method for preventing or treating a mycobacterium infection in a mammal comprising administering to a mammal in need of anti-mycobacterium prevention or treatment an effective anti-mycobacterium amount of at least one compound of formula ii:

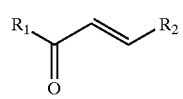

ii wherein $R_1$=4-fluorophenyl-, 3-hydroxyphenyl-, pyridin-3-yl-, furan-2-yl-, phenanthren-2-yl-, 3-fluorenyl-, pyridin-2-yl-, naphthalen-1-yl-, pyridin-2-yl-, 4-bromo-2-hydroxyphenyl-, pyridin-4-yl-, 2-hydroxy-4-methoxyphenyl-, 4-aminophenyl-, pyridin-4-yl-, 2-hydroxy-5-methoxyphenyl-, 4-methoxyphenyl-, 4-methoxyphenyl-, 2-hydroxy-5-chlorophenyl-, 4-aminophenyl-, 3-hydroxynaphthalen-2-yl-, furan-2-yl- or pyridin-2-yl-; and
  $R_2$=pyridin-3-yl-, phenanthren-9-yl-, phenanthren-9-yl-, phenyl-, 2-aminopyridino-3-yl, 2-aminopyridino-3-yl-, pyridin-2-yl-, phenyl-, 4-dimethylaminophenyl-, furan-2-yl-, indol-2-yl-, furan-2-yl-, 2-aminopyridin-3-yl-, 4-dimethylaminophenyl-, furan-2-yl-, pyridin-4-yl-, pyridin-3-yl-, 2-amino-pyridin-3-yl-, 2-aminopyridin-3-yl-, 2-aminopyridin-3-yl-, pyridin-4-yl- or 4-methoxyphenyl-; or
  a pharmaceutically acceptable derivative or salt thereof and a pharmaceutically acceptable carrier therefor.

2. The method of claim 1 wherein $R_1$=4-fluorophenyl- and $R_2$=pyridin-3-yl-.
3. The method of claim 1 wherein $R_1$=3-hydroxyphenyl- and $R_2$=phenanthren-9-yl-.
4. The method of claim 1 wherein $R_1$=pyridin-3-yl- and $R_2$=phenanthren-9-yl-.
5. The method of claim 1 wherein $R_1$=furan-2-yl- and $R_2$=phenyl-.
6. The method of claim 1 wherein $R_1$=phenanthren-2-yl and $R_2$=2-aminopyridino-3-yl-.
7. The method of claim 1 wherein $R_1$=3-fluorenyl- and $R_2$=2-aminopyridino-3-yl-.
8. The method of claim 1 wherein $R_1$=pyridin-2-yl- and $R_2$=pyridin-2-yl-.
9. The method of claim 1 wherein $R_1$=naphthalen-1-yl- and $R_2$=phenyl-.
10. The method of claim 1 wherein $R_1$=pyridin-2-yl- and $R_2$=4-dimethylaminophenyl-.
11. The method of claim 1 wherein $R_1$=4-bromo-2-hydroxyphenyl- and $R_2$=furan-2-yl-.
12. The method of claim 1 wherein $R_1$=pyridin-4-yl- and $R_2$=indol-2-yl-.
13. The method of claim 1 wherein $R_1$=2-hydroxy-4-methoxyphenyl-and $R_2$=furan-2-yl-.
14. The method of claim 1 wherein $R_1$=4-aminophenyl- and $R_2$=2-aminopyridin-3-yl-.
15. The method of claim 1 wherein $R_1$=pyridin-4-yl- and $R_2$=4-dimethylaminophenyl-.

* * * * *